(12) United States Patent
Gertler et al.

(10) Patent No.: US 10,114,023 B2
(45) Date of Patent: Oct. 30, 2018

(54) METHOD OF ENHANCING THE EFFICACY OF ANTI-HEPATOCYTE GROWTH FACTOR RECEPTOR BREAST CANCER THERAPY BY ADMINISTERING AN INHIBITOR OF MENA$^{INV}$

(71) Applicants: MASSACHUSETTS INSTITUTE OF TECHNOLOGY, Cambridge, MA (US); ALBERT EINSTEIN COLLEGE OF MEDICINE, INC., Bronx, NY (US)

(72) Inventors: Frank B. Gertler, Boston, MA (US); Shannon K. Hughes-Alford, Cambridge, MA (US); Douglas A. Lauffenburger, Cambridge, MA (US); Jason Neil, Jamaica Plain, MA (US); Forest White, Sutton, MA (US); John S. Condeelis, Bronx, NY (US); Madeleine J. Oudin, Cambridge, MA (US)

(73) Assignees: Massachusetts Institute of Technology, Cambridge, MA (US); Albert Einstein College of Medicine, Inc., Bronx, NY (US)

(*) Notice: Subject to any disclaimer, the term of this patent is extended or adjusted under 35 U.S.C. 154(b) by 0 days.

(21) Appl. No.: 14/390,113

(22) PCT Filed: Apr. 12, 2013

(86) PCT No.: PCT/US2013/036336
§ 371 (c)(1),
(2) Date: Oct. 2, 2014

(87) PCT Pub. No.: WO2013/158485
PCT Pub. Date: Oct. 24, 2013

(65) Prior Publication Data
US 2015/0044234 A1    Feb. 12, 2015

Related U.S. Application Data

(60) Provisional application No. 61/625,985, filed on Apr. 18, 2012, provisional application No. 61/778,767, filed on Mar. 13, 2013.

(51) Int. Cl.
| | |
|---|---|
| *G01N 33/574* | (2006.01) |
| *C12Q 1/42* | (2006.01) |
| *G01N 33/50* | (2006.01) |
| *G01N 33/68* | (2006.01) |
| *C07K 14/435* | (2006.01) |
| *C07K 16/18* | (2006.01) |
| *C12N 15/113* | (2010.01) |

(52) U.S. Cl.
CPC ..... *G01N 33/57492* (2013.01); *C07K 14/435* (2013.01); *C07K 16/18* (2013.01); *C12N 15/113* (2013.01); *C12Q 1/42* (2013.01); *G01N 33/5011* (2013.01); *G01N 33/6872* (2013.01); *C12N 2310/122* (2013.01); *C12N 2310/14* (2013.01); *C12N 2320/30* (2013.01); *G01N 2333/71* (2013.01); *G01N 2333/916* (2013.01); *G01N 2500/04* (2013.01); *G01N 2800/52* (2013.01)

(58) Field of Classification Search
CPC ........ C12Q 1/42; C07K 16/18; C07K 14/435; C12N 15/113; C12N 2310/122; C12N 2310/14; C12N 2320/30; G01N 33/5011; G01N 33/6872; G01N 33/57492; G01N 2500/04; G01N 2333/71; G01N 2333/916; G01N 2800/52
See application file for complete search history.

(56) References Cited

U.S. PATENT DOCUMENTS

| | | |
|---|---|---|
| 4,816,567 A | 3/1989 | Cabilly et al. |
| 5,530,101 A | 6/1996 | Queen et al. |
| 5,585,089 A | 12/1996 | Queen et al. |
| 5,693,761 A | 12/1997 | Queen et al. |
| 5,693,762 A | 12/1997 | Queen et al. |
| 5,807,715 A | 9/1998 | Morrison et al. |
| 5,866,692 A | 2/1999 | Shitara et al. |
| 5,939,598 A | 8/1999 | Kucherlapati et al. |
| 5,997,867 A | 12/1999 | Waldmann et al. |
| 6,054,297 A | 4/2000 | Carter et al. |
| 6,075,181 A | 6/2000 | Kucherlapati et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,180,370 B1 | 1/2001 | Queen et al. |
| 6,180,377 B1 | 1/2001 | Morgan et al. |

(Continued)

FOREIGN PATENT DOCUMENTS

| | | |
|---|---|---|
| EP | 0519596 | 12/1992 |
| WO | WO 1999/058572 | 11/1999 |

(Continued)

OTHER PUBLICATIONS

Roussos ET, et al. J Cell Sci. 124(13): 2120-2131. Jul. 1, 2011. Available online at—doi: 10.1242/jcs.086231.*

(Continued)

*Primary Examiner* — Robert S Landsman
(74) *Attorney, Agent, or Firm* — Bryan D. Zerhusen; Cantor Colburn LLP

(57) ABSTRACT

Methods and compositions are provided for diagnosing or inhibiting invasion or metastasis of a cancer in a subject based on Mena$^{INV}$.

4 Claims, 20 Drawing Sheets
Specification includes a Sequence Listing.

(56) References Cited

U.S. PATENT DOCUMENTS

| | | |
|---|---|---|
| 6,210,671 B1 | 4/2001 | Co |
| 6,331,415 B1 | 12/2001 | Cabilly et al. |
| 6,350,861 B1 | 2/2002 | Co et al. |
| 6,982,321 B2 | 1/2006 | Winter et al. |
| 7,087,409 B2 | 8/2006 | Barbas et al. |
| 8,603,738 B2 | 12/2013 | Condeelis et al. |
| 9,719,142 B2 | 8/2017 | Condeelis et al. |
| 2002/0055109 A1 | 5/2002 | Thill |

FOREIGN PATENT DOCUMENTS

| | | |
|---|---|---|
| WO | WO 2001/027160 | 4/2001 |
| WO | WO 2002/043478 | 6/2002 |
| WO | WO 2008/097466 | 8/2008 |
| WO | 2011076095 A1 | 6/2011 |
| WO | 2011093989 A1 | 8/2011 |

OTHER PUBLICATIONS

Philippar U, et al. Dev. Cell. 15(6): 813-828. Dec. 2008. Available online at—doi:10.1016/j.devcel1.2008.09.003.*
Roussos ET, et al. Breast Cancer Research. 12:R101-116, 2010.*
Tyan S-W, et al. PLoS ONE. 6(1). Jan. 2011.*
NCIC Clinical Trials Group. Clinical Trials.gov. Trial No. NCT01147484.*
Winer EP, et al. Annual Meeting of the American Society of Clinical Oncology. Poster #535. Chicago, IL. Jun. 1-5, 2012.*
PCT International Search Report and Written Opinion, dated Sep. 20, 2013 in connection with PCT International Application No. PCT/US2013/36336, 19 pages.
Albiges-Rizo C et al., entitled "Actin machinery and mechanosensitivity in invadopodia, podosomes and focal adhesions," Journal of Cell Science, 209, vol. 122, No. 17, pp. 3037-3049, 2009.
Bird, et al., Science, 242:423-426 (1988).
Boerner, et al., J. Immunol., 147(1):86-95 (1991).
Brown, et al., Cancer Res. 47: 3577-3583 (1987).
Chothia & Lesk, J. Mol. Biol. 196:901-917 (1987).
Chothia, et al., Nature 342:878-883 (1989).
Cole, et al., Monoclonal Antibodies and Cancer Therapy, Alan R. Liss, p. 77 (1985).
Daugherty, et al., Nucl. Acids Res. 19: 2471-2476 (1991).
Di Modugno, et al., "The Cytoskeleton Regulatory Protein hMena (ENAH) is Overepress in Human Benign Breast Lesions with High Risk of Transformation and Human Epidermal Growth Factor Receptor-2-Positive/Hormonal Receptor—Negaive Tumors", Clinical Cancer Research 2006; 12(5) Mar. 1, 2006, 1470-1478.
Gertler, et al. Genbank 1996, "Mus Musculus Neural Variant Mena+++ Protein (Mena) mRNA, complete cds", http://www.ncbi.nlm.nih.gov/nucore/U72523.
Gertler, F.B. et al, "Mena a relative of VASP and drosophila enabled, is implicated in the control of microfilament dynamics" Cell, 1996 87(2): p. 227-39.
Goswami, et al., "Identification of invation specific splice variants of the cytoskeletal protein Mena present in mammary tumor cells during invasion in vivo", Cln. Exp Metastasis, 2009, 26(2): p. 153-9.
Haj, et al., Regulation of receptor tyrosine kinase signaling by protein tyrosine phosphatase-1B. J Biol Chem, 2003. 278(2): p. 739-44.
Hamers-Casterman, et al., Nature 363:446-448 (1993).
Harris, Biochem. Soc.Transactions 23:1035-1038 (1995).
Hoogenboom and Winter, J. Mol. Biol., 227:381 (1991).
Hurle and Gross, Curr. Op. Biotech. 5:428-433 (1994).
Huston, et al., Proc. Natl. Acad. Sci. USA, 85:5879-5883 (1988).
Johnson and Wu, Methods in Microbiology 248:1-25 (Lo, ed., Human Press, Totowa, NJ, 2003).
Jones, et al., Nature 321:522-525 (1986).
Li, et al., Proc. Natl. Acad. Sci. USA, 103:35573562 (2006).
Lobuglio, et al., Proc. Nat. Acad. Aci. USA 86: 4220-4224 (1989).
Marks, et al., J. Mol. Biol., 222:581 (1991).
NEB Catalog 1998/1999, New England Biolabs, Inc. (pp. 121 and 284).
Presta, Curr. Op. Struct. Biol. 2:593-596 (1992).
Riechmann, et al., Nature 332:323-329 (1988).
Roussos, et al., Mena invasive (Mena(INV)) and Mena1 1a isoforms play distinct roles in breast cancer cell cohesion an associated with TMEM. Clin Exp, Metastasis, 2011, 28(6): p. 515-27.
Shaw, et al., J. Immunol. 138: 4534-4538 (1987).
Sheriff, et al., Nature Struct. Biol. 3:733-736 (1996).
Soderberg, et al., "Characterizing proteins and their interactions in cells an dtissues using the in situ proximity ligation assay", Methods, 2008 45(3): p. 227-32.
Tomizuka, et al., Proc. Natl., Acad. Sci. USA 97:722-727 (2000).
Urbanelli, et al., "Characterization of human Enah gene", Biochimica et Biophysica Acta 1759 (2006) 99-107.
Van Dijk and van de Winkel, Curr. Opin. Pharmacol., 5:386-74 (2001).
Vaswani and Hamilton, Ann. Allergy, Asthma & Immunol. 1:105-115 (1998).
Verhoeyen, et al., Science 239: 1534-1536 (1988).
Ward, et al., Nature 341:544-546 (1989).
Winter, et al., Nature 349:293-299 (1991).
Xu, et al., Immunity 13:37-45 (2000).

* cited by examiner

[A]

SYYTVRQLELENLTTQETREILHFH
RQLELENLTTQETREILHFHYTTWP
ENLTTQETREILHFHYTTWPDFGVP
QETREILHFHYTTWPDFGVPESPAS
ILHFHYTTWPDFGVPESPASFLNFL
YTTWPDFGVPESPASFLNFLFKVRE
DFGVPESPASFLNFLFKVRESGSLS

IMGDSSVQDQWKELSHEDLEPPPEH
SVQDQWKELSHEDLEPPPEHIPPPP
WKELSHEDLEPPPEHIPPPPRPPKR
HEDLEPPPEHIPPPPRPPKRILEPH
PPPEHIPPPPRPPKRILEPHNGKCR
IPPPPRPPKRILEPHNGKCREFFPN
ASDFPPPPTDEELRLALPETPMLLG

[B]
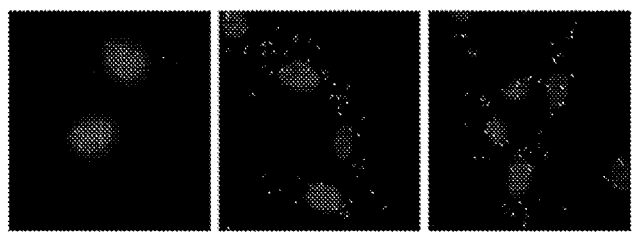

[C]
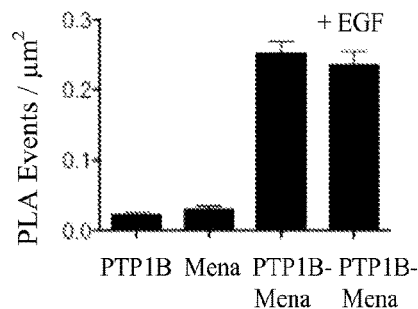

METHOD OF ENHANCING THE EFFICACY OF ANTI-HEPATOCYTE GROWTH FACTOR RECEPTOR BREAST CANCER THERAPY BY ADMINISTERING AN INHIBITOR OF MENA$^{INV}$

CROSS-REFERENCE TO RELATED APPLICATIONS

This application is a U.S. national stage entry under 35 U.S.C. §371 of PCT International Patent Application No. PCT/US2013/36336, filed Apr. 12, 2013, which claims benefit of U.S. Provisional Application No. 61/625,985, filed Apr. 18, 2012 and U.S. Provisional Application No. 61/778,767, filed Mar. 13, 2013 the contents of each of which are hereby incorporated by reference.

STATEMENT OF GOVERNMENT SUPPORT

This invention was made with government support under Grant Nos. R01 GM081336, R01 GM058801 and U54 CA112967 awarded by the National Institutes of Health and under Grant No. W81XWH-10-1-0040 awarded by the US Army MRMC. The Government has certain rights in the invention.

BACKGROUND OF THE INVENTION

Throughout this application various publications, books, patents and patent application publications are referred to. The disclosures of all of these are hereby incorporated by reference in their entireties into the subject application to more fully describe the art to which the subject application pertains.

Cancer cell invasion and metastasis remain a significant health problem and complicate the decisions regarding therapy for cancer sufferers. The roles for different isoforms of Mena in cancer cell invasion and in metastasis are not fully understood.

The present invention addresses the need for improved treatments, diagnostic tests and assays based on the roles disclosed herein for Mena$^{INV}$ in cancer invasion and metastasis.

SUMMARY OF THE INVENTION

A method is provided of identifying an agent as an inhibitor of sarcoma or carcinoma cell invasion or as an inhibitor of metastasis of a carcinoma or sarcoma, comprising contacting a preparation comprising a growth factor receptor and a protein-tyrosine phosphatase 1b (PTP1b) in the presence of an amount of Mena$^{INV}$ and an amount of Mena and quantifying the association of the growth factor receptor and PTP1b in the presence of the agent and in the absence of the agent, wherein an agent that increases the association of growth factor receptor and PTP1b in the presence of the agent as compared to in the absence of the agent is identified as an inhibitor of sarcoma or carcinoma cell invasion or of metastasis, and an agent that does not increase, or decreases, the association of growth factor receptor and PTP1b in the presence of the agent as compared to in the absence of the agent is not identified as an inhibitor of sarcoma or carcinoma cell invasion or metastasis.

A method is also provided of identifying an agent as a sensitizer of a growth factor receptor-expressing carcinoma cell to a corresponding growth factor or as a dysregulator of a PTP1b-binding growth factor receptor, comprising contacting a preparation comprising a growth factor receptor and a protein-tyrosine phosphatase 1b (PTP1b) in the presence of an amount of MenaINV and an amount of Mena and quantifying the association of the growth factor receptor and PTP1b in the presence of the agent and in the absence of the agent, wherein an agent that decreases the association of growth factor receptor and PTP1b as compared to the association in the absence of the agent is identified as a sensitizer of a growth factor receptor-expressing carcinoma cell to the corresponding growth factor or as a dysregulator, and an agent that does not change or that increases the association of growth factor receptor and PTP1b as compared to the association in the absence of the agent is not identified as a sensitizer of the growth factor receptor-expressing carcinoma cell to the corresponding growth factor or a dysregulator.

A method is also provided of identifying an agent as an inhibitor of sarcoma or carcinoma cell invasion or of metastasis of a carcinoma or sarcoma, the method comprising contacting a preparation comprising a protein-tyrosine phosphatase 1b (PTP1b) with the agent in the presence of an amount of Mena$^{INV}$ and an amount of Mena and quantifying the association of (i) Mena$^{INV}$ and PTP1b, and of (ii) Mena and PTP1b, wherein an agent that increases the association of Mena with PTP1b relative to the association of Mena$^{INV}$ with PTP1b as compared to such associations in the absence of the agent is identified as an inhibitor of sarcoma or carcinoma cell invasion or metastasis, and wherein an agent that does not affect, or which decreases, the association of Mena with PTP1b relative to the association of Mena$^{INV}$ with PTP1b as compared to such associations in the absence of the agent is not identified as an inhibitor of sarcoma or carcinoma cell invasion or metastasis.

A further method is provided of identifying an agent as an inhibitor of sarcoma or carcinoma cell invasion or of metastasis of a carcinoma or sarcoma, the method comprising contacting a preparation comprising an amount of Mena$^{INV}$, an amount of Mena, and a protein listed in the "Protein" column of Table 1, wherein the protein is phosphorylated at the site or sites listed in the "Abrev/Site" column of Table 1, with the agent and protein-tyrosine phosphatase 1b (PTP1b) and quantifying phosphorylation of the protein at the site or sites,
wherein a decrease in phosphorylation in (a) the presence of the agent and PTP1b as compared to (b) in the absence of the agent and presence of PTP1b identifies the agent as an inhibitor of sarcoma or carcinoma cell invasion or metastasis, and wherein an increase in, or no change in, phosphorylation in (i) the presence of the agent and PTP1b as compared to (ii) in the absence of the agent and presence of PTP1b does not identify the agent as an inhibitor of sarcoma or carcinoma cell invasion or metastasis.

A method is also provided of determining the efficacy of a cancer therapy on a Mena$^{INV}$-expressing cancer comprising quantifying Mena$^{INV}$ or PTP1b in a plurality of biological samples from a subject having the cancer, wherein the samples are obtained from the subject at different time points, and wherein a first sample is obtained either before commencement of therapy or during therapy and wherein at least a second sample is obtained later in the therapy than the first sample or subsequent to the therapy, wherein a decrease in the Mena$^{INV}$, or increase in PTP1b, quantified in the second sample as compared to the first sample indicates that the therapy is efficacious on the Mena$^{INV}$-expressing cancer, and wherein no change in, or an increase in, the Mena$^{INV}$, or a decrease in PTP1B, quantified in the second sample as compared to the first sample indicates that the therapy is not efficacious on the Mena$^{INV}$-expressing cancer.

A method is also provided of diagnosing a subject having a cancer as suitable for receiving a cancer therapy comprising inhibition of Mena$^{INV}$, the method comprising quantifying Mena$^{INV}$ or PTP1b in a biological sample from the cancer and comparing the Mena$^{INV}$ or PTP1b quantified therein to a predetermined control amount of Mena$^{INV}$ or PTP1b, respectively, wherein an amount of Mena$^{INV}$ quantified in the sample less than or equal to the control amount, or an amount of PTP1b equal to or more than the control amount, indicates that the subject is not suitable for a therapy comprising inhibition of Mena$^{INV}$, and wherein an amount of Mena$^{INV}$ quantified in the sample greater than the control amount, or an amount of PTP1b less than the control amount, indicates that the subject is suitable for receiving a therapy comprising inhibition of Mena$^{INV}$.

A method is also provided of enhancing the efficacy of an anti-growth factor receptor cancer therapy on a subject comprising administering to the subject an amount of an inhibitor of Mena$^{INV}$ effective to enhance the efficacy of an the anti-growth factor receptor cancer therapy.

Also provided is a composition comprising an amount of an inhibitor of Mena$^{INV}$ and an anti-growth factor receptor pharmaceutical. In an embodiment, the inhibitor of Mena$^{INV}$ is an antibody, an antibody fragment, a small organic molecule of less than 2000 daltons, an siRNA or a shRNA. In an embodiment, the anti-growth factor receptor pharmaceutical is an EGFR kinase inhibitor. In an embodiment, the anti-growth factor receptor pharmaceutical is erlotinib or gefitnib. In an embodiment, the composition further comprises a pharmaceutically acceptable carrier.

A method is also provided of identifying an agent as an inhibitor of sarcoma or carcinoma cell invasion or as an inhibitor of metastasis of a carcinoma or sarcoma, comprising contacting a preparation comprising SHIP2 (IPPL1) and an amount of Mena$^{INV}$ in the presence of the agent and in the absence of the agent, wherein an agent that decreases the activation of SHIP2 by Mena$^{INV}$ is identified as an inhibitor of sarcoma or carcinoma cell invasion or of metastasis, and an agent that increases, or does not change, the activation of SHIP2 by Mena$^{INV}$ is not identified as an inhibitor of sarcoma or carcinoma cell invasion or metastasis. In an embodiment, the preparation also comprises a protein-tyrosine phosphatase 1b (PTP1b).

Also provided is a method of determining the efficacy of a cancer therapy on a Mena$^{INV}$-expressing cancer comprising quantifying activated SHIP2 or SHIP2 product(s) in a plurality of biological samples from a subject having the cancer, wherein the samples are obtained from the subject at different time points, and wherein a first sample is obtained either before commencement of therapy or during therapy and wherein at least a second sample is obtained later in the therapy than the first sample or subsequent to the therapy, wherein a decrease in the activated SHIP2 or SHIP2 product(s) quantified in the second sample as compared to the first sample indicates that the therapy is efficacious on the Mena$^{INV}$-expressing cancer, and wherein no change in, or an increase in, the activated SHIP2 or SHIP2 product(s) quantified in the second sample as compared to the first sample indicates that the therapy is not efficacious on the Mena$^{INV}$-expressing cancer.

Also provided is a method of diagnosing a subject having a cancer as suitable for receiving a cancer therapy comprising inhibition of Mena$^{INV}$, the method comprising quantifying activated SHIP2 or SHIP2 product(s) in a biological sample from the cancer and comparing the activated SHIP2 or SHIP2 product(s) quantified therein to a predetermined control amount of activated SHIP2 or SHIP2 product(s), respectively, wherein an amount of activated SHIP2 or SHIP2 product(s) quantified in the sample less than or equal to the control amount, indicates that the subject is not suitable for a therapy comprising inhibition of Mena$^{INV}$, and wherein an amount of activated SHIP2 or SHIP2 product(s) quantified in the sample greater than the control amount, indicates that the subject is suitable for receiving a therapy comprising inhibition of Mena$^{INV}$.

Also provided is a method of diagnosing a subject as having a cancer likely to metastasize comprising quantifying the phosphorylation status of 5 or more of the proteins listed in Table 1 in a cancer sample obtained from the subject, wherein a level of phosphorylation quantified therein greater than a predetermined control amount of phosphorylation for each protein indicates that the subject has a cancer likely to metastasize, and wherein a level of phosphorylation quantified therein less than the predetermined control amount of phosphorylation for each protein does not indicate that the subject has a cancer likely to metastasize.

Also provided is a method of diagnosing a subject as suitable for receiving a cancer therapy comprising inhibition of Mena$^{INV}$, the method comprising quantifying the phosphorylation status of 5 or more of the proteins listed in Table 1 in a cancer sample obtained from the subject, wherein a level of phosphorylation quantified therein greater than a predetermined control amount of phosphorylation for each protein indicates that the subject is suitable for receiving a cancer therapy, and wherein a level of phosphorylation quantified therein less than the predetermined control amount of phosphorylation for each protein does not indicate that the subject is suitable for receiving a cancer therapy.

BRIEF DESCRIPTION OF THE FIGURES

FIG. 1A-C. Mena and PTP1b directly interact within intact cells. A walk-through peptide array of PTP1b was created using 25-mer peptides and overlayed with recombinant Mena EVH-1 domain to determine direct binding between Mena and PTP1b (A) (SEQ ID NOS: 1-14, left hand column top to bottom, then right hand column top to bottom, respectively). Dark spots reveal regions of interaction. The right-most lower spot is a positive FPPPP control peptide from a known Mena binding partner, ActA. Mena EVH-1 binds both a canonical-like sequence of PTP1b (IPPPP, right side) and a non-canonical sequence (left side). (B) Unmodified MDA-MB231 lysate was probed with recombinant GST-(Mena)EVH1 domain or a GST-control. PTP1b bound to the Mena EVH1 domain illustrating interaction between Mena and PTP1b in MDA-MB231 cell lysate. (C) PLA was utilized to measure Mena-PTP1b complex formation within intact cells. Ena/VASP-null cells (Mena−/−) were employed as a negative control. The Mena-PTP1b complex is independent of EGF stimulation FIG. 2A-2G. Inhibition of PTP1b phenocopies expression of Mena$^{INV}$. (A) MDA-MB231 cells were serum starved for 4 h with addition of 10 μM PTP1b inhibitor (EMD Calbiochem) for the time indicated. Cells were then stimulated with 0.5 nM EGF and lamellipodial protrusion was measured 8 min post-stimulation. A 30 min pre-incubation with PTP1bi resulted in a significant increase in membrane protrusion in GFP-control cells to levels measured in cells expressing Mena$^{INV}$. The kinetics of protrusion (B) were also increased upon a 30 min pre-incubation with PTP1bi. Importantly, protrusion was increased in cells expressing GFP-Mena at 0.25 nM EGF (C), but no further increase was measured in cells expressing Mena$^{INV}$ suggesting that the PTP1b dysregulation is specific to the inclusion of the INV exon. Lamellipodial protrusion was significantly enhanced at 0.5 nM EGF in unmodified MTLn3 cells upon PTP1b inhibition (D) illustrating that the effect is not cell-type specific or retrovirally induced. In vitro invasion into 2.3 mg/mL collagen I gels (E,F) was also increased upon PTP1b inhibition in GFP-control and GFP-Mena expressing cells, but not in cells expressing Mena$^{INV}$. (G) Inhibition of PTP1b in vivo shifts the sensitivity of GFP-Control MTLn3 xenografted cells to 5 nM (a 5× increase in sensitivity). *p<0.05 and **p<0.01 by ANOVA and Tukey post-test.

DETAILED DESCRIPTION OF THE INVENTION

Figures 2A, 2B, 2C, 2D, 2E, 2F:
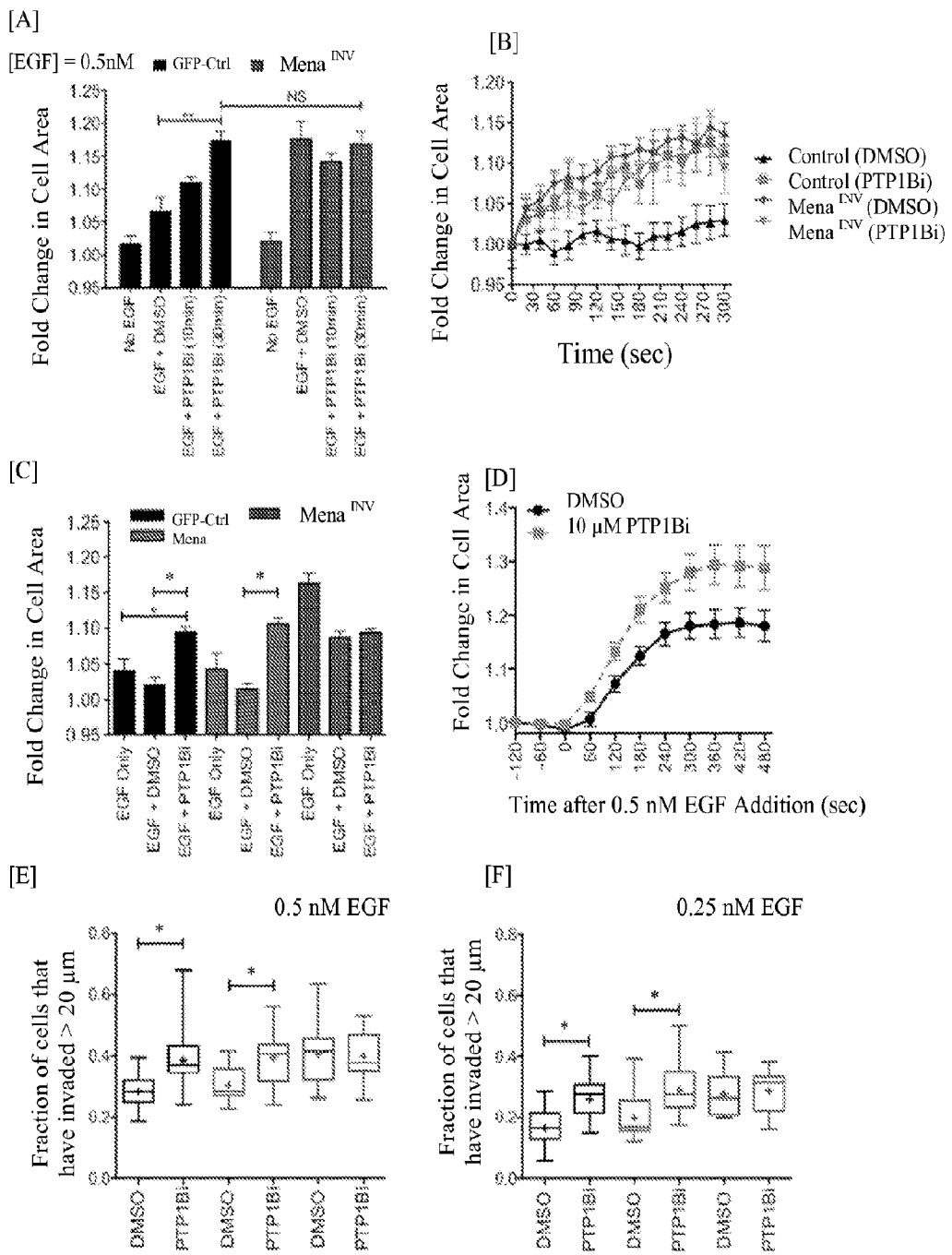

A method is provided of identifying an agent as an inhibitor of sarcoma or carcinoma cell invasion or as an inhibitor of metastasis of a carcinoma or sarcoma, comprising contacting a preparation comprising a growth factor receptor and a protein-tyrosine phosphatase 1b (PTP1b) in the presence of an amount of Mena$^{INV}$ and an amount of Mena and quantifying the association of the growth factor receptor and PTP1b in the presence of the agent and in the absence of the agent, wherein an agent that increases the association of growth factor receptor and PTP1b in the presence of the agent as compared to in the absence of the agent is identified as an inhibitor of sarcoma or carcinoma cell invasion or of metastasis, and an agent that does not increase, or decreases, the association of growth factor receptor and PTP1b in the presence of the agent as compared to in the absence of the agent is not identified as an inhibitor of sarcoma or carcinoma cell invasion or metastasis.

In an embodiment, the growth factor receptor is a PTP1b-interacting growth factor receptor.

A method is also provided of identifying an agent as a sensitizer of a growth factor receptor-expressing carcinoma cell to a corresponding growth factor or as a dysregulator of a PTP1b-binding growth factor receptor, comprising contacting a preparation comprising a growth factor receptor and a protein-tyrosine phosphatase 1b (PTP1b) in the presence of an amount of Mena$^{INV}$ and an amount of Mena and quantifying the association of the growth factor receptor and PTP1b in the presence of the agent and in the absence of the agent, wherein an agent that decreases the association of growth factor receptor and PTP1b as compared to the association in the absence of the agent is identified as a sensitizer of a growth factor receptor-expressing carcinoma cell to the corresponding growth factor or as a dysregulator, and an agent that does not change or that increases the association of growth factor receptor and PTP1b as compared to the association in the absence of the agent is not identified as a sensitizer of the growth factor receptor-expressing carcinoma cell to the corresponding growth factor or a dysregulator.

In an embodiment of the methods, the growth factor receptor is an epithelial growth factor receptor (EGFR). In an embodiment of the methods, the growth factor receptor is a hepatoctye growth factor receptor (HGFR or MET). In an embodiment of the methods, the growth factor receptor is a receptor for IGF, AXL, HB-EGF, AREG or NRG. In an embodiment of the methods, the growth factor receptor is expressed by a tumor cell or on a tumor cell line. In an embodiment of the methods, the Mena$^{INV}$ is expressed by a tumor cell or by a cell of a tumor cell line. In an embodiment of the methods, a cell of the carcinoma expresses Mena$^{INV}$. In an embodiment of the methods, the association of PTP1b and the growth factor receptor is quantified using a proximity ligation association assay. In an embodiment the methods further comprise stimulating the growth factor receptor.

A method is also provided of identifying an agent as an inhibitor of sarcoma or carcinoma cell invasion or of metastasis of a carcinoma or sarcoma, the method comprising contacting a preparation comprising a protein-tyrosine phosphatase 1b (PTP1b) with the agent in the presence of an amount of Mena$^{INV}$ and an amount of Mena and quantifying the association of (i) Mena$^{INV}$ and PTP1b, and of (ii) Mena and PTP1b, wherein an agent that increases the association of Mena with PTP1b relative to the association of Mena$^{INV}$ with PTP1b as compared to such associations in the absence of the agent is identified as an inhibitor of sarcoma or carcinoma cell invasion or metastasis, and wherein an agent that does not affect, or which decreases, the association of Mena with PTP1b relative to the association of Mena$^{INV}$ with PTP1b as compared to such associations in the absence of the agent is not identified as an inhibitor of sarcoma or carcinoma cell invasion or metastasis.

In an embodiment of the method, the Mena$^{INV}$ is expressed by a tumor cell or by a tumor cell line. In an embodiment of the methods, a cell of the sarcoma or carcinoma expresses Mena$^{INV}$. In an embodiment of the method, the agent inhibits the binding of Mena$^{INV}$ to one or more of SEQ ID NOS:3, 11 and 14. In an embodiment of the method, the agent binds to Mena$^{INV}$ but not Mena. In an embodiment of the method, the association of each of (i) Mena$^{INV}$ with PTP1b, and of (ii) Mena with PTP1b, is determined using a proximity ligation association assay.

A further method is provided of identifying an agent as an inhibitor of sarcoma or carcinoma cell invasion or of metastasis of a carcinoma or sarcoma, the method comprising contacting a preparation comprising an amount of Mena$^{INV}$, an amount of Mena, and a protein listed in the "Protein" column of Table 1, wherein the protein is phosphorylated at the site or sites listed in the "Abrev/Site" column of Table 1, with the agent and protein-tyrosine phosphatase 1b (PTP1b) and quantifying phosphorylation of the protein at the site or sites, wherein a decrease in phosphorylation in (a) the presence of the agent and PTP1b as compared to (b) in the absence of the agent and presence of PTP1b identifies the agent as an inhibitor of sarcoma or carcinoma cell invasion or metastasis, and wherein an increase in, or no change in, phosphorylation in (i) the presence of the agent and PTP1b as compared to (ii) in the absence of the agent and presence of PTP1b does not identify the agent as an inhibitor of sarcoma or carcinoma cell invasion or metastasis.

In an embodiment of the method, a cell of the sarcoma or carcinoma expresses Mena$^{INV}$.

In an embodiment of the methods disclosed herein, the Mena$^{INV}$ is a human Mena$^{INV}$. In an embodiment of the methods disclosed herein, the Mena is a human Mena. In an embodiment of the methods disclosed herein, the agent is a small organic molecule of 2000 daltons or less, an antibody, an antibody fragment, a fusion protein or peptide, an RNAi agent or an aptamer. In an embodiment of the methods disclosed herein, the agent is an RNAi agent and is an siRNA or a shRNA. In an embodiment of the methods disclosed herein, the carcinoma is a mammary carcinoma.

A method is also provided of determining the efficacy of a cancer therapy on a Mena$^{INV}$-expressing cancer comprising quantifying Mena$^{INV}$ or PTP1b in a plurality of biological samples from a subject having the cancer, wherein the samples are obtained from the subject at different time points, and wherein a first sample is obtained either before commencement of therapy or during therapy and wherein at least a second sample is obtained later in the therapy than the first sample or subsequent to the therapy, wherein a decrease in the Mena$^{INV}$, or increase in PTP1b, quantified in the second sample as compared to the first sample indicates that the therapy is efficacious on the Mena$^{INV}$-expressing cancer, and wherein no change in, or an increase in, the Mena$^{INV}$, or a decrease in PTP1B, quantified in the second sample as compared to the first sample indicates that the therapy is not efficacious on the Mena$^{INV}$-expressing cancer.

A method is also provided of diagnosing a subject having a cancer as suitable for receiving a cancer therapy comprising inhibition of Mena$^{INV}$, the method comprising quantifying Mena$^{INV}$ or PTP1b in a biological sample from the cancer and comparing the Mena$^{INV}$ or PTP1b quantified therein to a predetermined control amount of Mena$^{INV}$ or PTP1b, respectively, wherein an amount of Mena$^{INV}$ quantified in the sample less than or equal to the control amount, or an amount of PTP1b equal to or more than the control amount, indicates that the subject is not suitable for a therapy comprising inhibition of Mena$^{INV}$, and wherein an amount of Mena$^{INV}$ quantified in the sample greater than the control amount, or an amount of PTP1b less than the control amount, indicates that the subject is suitable for receiving a therapy comprising inhibition of Mena$^{INV}$.

In an embodiment, the subject has previously received a growth factor receptor tyrosine kinase inhibitor. In an embodiment, the Mena$^{INV}$ is quantified in the sample using an enzyme-linked immunosorbent assay (ELISA), a western blot, immunological staining. In an embodiment, the sample is a sarcoma or carcinoma cell lysate sample. In an embodiment, the cancer therapy comprises an anti-EGFR therapy. In an embodiment, the cancer therapy comprises an anti-HGFR therapy/anti-MET tyrosine kinase therapy. In an embodiment of the methods, the cancer therapy comprises an inhibitor of a receptor for IGF, AXL, HB-EGF, AREG or NRG.

A method of treating a subject for a cancer is also provided, comprising diagnosing the subject as suitable for receiving an anti-cancer therapy by any of the diagnostic methods disclosed herein and, and a subject so diagnosed as having a cancer as suitable for receiving a cancer therapy comprising inhibition of Mena$^{INV}$, administering to the subject a cancer therapy comprising inhibition of Mena$^{INV}$ effective to treat a cancer.

A method is also provided of enhancing the efficacy of an anti-growth factor receptor cancer therapy on a subject comprising administering to the subject an amount of an inhibitor of Mena$^{INV}$ effective to enhance the efficacy of an the anti-growth factor receptor cancer therapy.

In an embodiment, the anti-growth factor receptor cancer therapy is an anti-epithelial growth factor receptor therapy. In an embodiment, the therapy is erlotinib therapy or gefitnib therapy. In an embodiment, the anti-growth factor receptor cancer therapy is an anti-HGFR therapy/anti-MET tyrosine kinase therapy. In an embodiment, the therapy is cabozantinib therapy or foretinib therapy. In an embodiment, the therapy comprises an inhibitor of a receptor for IGF, AXL, HB-EGF, AREG or NRG. In an embodiment, the cancer is a mammary cancer. In an embodiment, the inhibitor of Mena$^{INV}$ is administered directly into a tumor of the cancer. In an embodiment, the inhibitor of Mena$^{INV}$ is an RNAi nucleic acid directed at Mena$^{INV}$. In an embodiment, the inhibitor of Mena$^{INV}$ is an siRNA or a shRNA. In an embodiment, the Mena$^{INV}$ is a human Mena$^{INV}$. In an embodiment, the therapy increases association of PTP1b with an EGFR in the subject. In an embodiment, the therapy increases association of PTP1b with an HGFR or MET in the subject.

Also provided is a composition comprising an amount of an inhibitor of Mena$^{INV}$ and an anti-growth factor receptor pharmaceutical. In an embodiment, the inhibitor of Mena$^{INV}$ is an antibody, an antibody fragment, a small organic molecule of less than 2000 daltons, an siRNA or a shRNA. In an embodiment, the anti-growth factor receptor pharmaceutical is an EGFR kinase inhibitor. In an embodiment, the anti-growth factor receptor pharmaceutical is erlotinib or gefitnib. In an embodiment, the anti-growth factor receptor pharmaceutical is an anti-HGFR therapeutic/anti-MET tyrosine kinase therapeutic. In an embodiment, the anti-growth factor receptor pharmaceutical is cabozantinib or foretinib. In an embodiment, the anti-growth factor receptor pharmaceutical comprises an inhibitor of a receptor for IGF, AXL, HB-EGF, AREG or NRG. In an embodiment, the composition further comprises a pharmaceutically acceptable carrier.

A method is also provided of identifying an agent as an inhibitor of sarcoma or carcinoma cell invasion or as an inhibitor of metastasis of a carcinoma or sarcoma, comprising contacting a preparation comprising SHIP2 (IPPL1) and an amount of Mena$^{INV}$ in the presence of the agent and in the absence of the agent, wherein an agent that decreases the activation of SHIP2 by Mena$^{INV}$ is identified as an inhibitor of sarcoma or carcinoma cell invasion or of metastasis, and an agent that increases, or does not change, the activation of SHIP2 by Mena$^{INV}$ is not identified as an inhibitor of sarcoma or carcinoma cell invasion or metastasis. In an embodiment, the preparation also comprises a protein-tyrosine phosphatase 1b (PTP1b).

Also provided is a method of determining the efficacy of a cancer therapy on a Mena$^{INV}$-expressing cancer comprising quantifying activated SHIP2 or SHIP2 product(s) in a plurality of biological samples from a subject having the cancer, wherein the samples are obtained from the subject at different time points, and wherein a first sample is obtained either before commencement of therapy or during therapy and wherein at least a second sample is obtained later in the therapy than the first sample or subsequent to the therapy, wherein a decrease in the activated SHIP2 or SHIP2 product(s) quantified in the second sample as compared to the first sample indicates that the therapy is efficacious on the Mena$^{INV}$-expressing cancer, and wherein no change in, or an increase in, the activated SHIP2 or SHIP2 product(s) quantified in the second sample as compared to the first sample indicates that the therapy is not efficacious on the Mena$^{INV}$-expressing cancer.

Also provided is a method of diagnosing a subject having a cancer as suitable for receiving a cancer therapy comprising inhibition of Mena$^{INV}$, the method comprising quantifying activated SHIP2 or SHIP2 product(s) in a biological sample from the cancer and comparing the activated SHIP2 or SHIP2 product(s) quantified therein to a predetermined control amount of activated SHIP2 or SHIP2 product(s), respectively, wherein an amount of activated SHIP2 or SHIP2 product(s) quantified in the sample less than or equal to the control amount, indicates that the subject is not suitable for a therapy comprising inhibition of Mena$^{INV}$, and wherein an amount of activated SHIP2 or SHIP2 product(s) quantified in the sample greater than the control amount, indicates that the subject is suitable for receiving a therapy comprising inhibition of Mena$^{INV}$.

Also provided is a method of diagnosing a subject as having a cancer likely to metastasize comprising quantifying the phosphorylation status of 5 or more of the proteins listed in Table 1 in a cancer sample obtained from the subject, wherein a level of phosphorylation quantified therein greater than a predetermined control amount of phosphorylation for each protein indicates that the subject has a cancer likely to metastasize, and wherein a level of phosphorylation quantified therein less than the predetermined control amount of phosphorylation for each protein does not indicate that the subject has a cancer likely to metastasize. In embodiments, the method is also provided comprising quantifying the phosphorylation status of 10 or more, 15 or more or 20 or more of the proteins listed in Table 1. In embodiments, the phosphorylation is determined for the sites listed in Table 1.

Also provided is a method of diagnosing a subject as suitable for receiving a cancer therapy comprising inhibition of Mena$^{INV}$, the method comprising quantifying the phosphorylation status of 5 or more of the proteins listed in Table 1 in a cancer sample obtained from the subject, wherein a level of phosphorylation quantified therein greater than a predetermined control amount of phosphorylation for each protein indicates that the subject is suitable for receiving a cancer therapy, and wherein a level of phosphorylation quantified therein less than the predetermined control amount of phosphorylation for each protein does not indicate that the subject is suitable for receiving a cancer therapy. In embodiments, the method is also provided comprising quantifying the phosphorylation status of 10 or more, 15 or more or 20 or more of the proteins listed in Table 1. In embodiments, the phosphorylation is determined for the sites listed in Table 1.

Protein-tyrosine phosphatase 1b (PTP1b) is an enzyme member of the protein tyrosine phosphatase (PTP) family. In an embodiment, the PTP1b is encoded by the human PTPN1 gene. In an embodiment, the PTP1b is a mammalian human PTP1b. In an embodiment, the PTP1b is a human PTP1b. In an embodiment, PTP1b comprises the sequence:

```
                                        (SEQ ID NO: 17)
MEMEKEFEQI DKSGSWAAIY QDIRHEASDF PCRVAKLPKN

KNRNRYRDVS PFDHSRIKLH QEDNDYINAS LIKMEEAQRS

YILTQGPLPN TCGHFWEMVW EQKSRGVVML NRVMEKGSLK

CAQYWPQKEE KEMIFEDTNL KLTLISEDIK SYYTVRQLEL

ENLTTQETRE ILHFHYTTWP DFGVPESPAS FLNFLFKVRE

SGSLSPEHGP VVVHCSAGIG RSGTFCLADT CLLLMDKRKD

PSSVDIKKVL LEMRKFRMGL IQTADQLRFS YLAVIEGAKF

IMGDSSVQDQ WKELSHEDLE PPPEHIPPPP RPPKRILEPH

NGKCREFFPN HQWVKEETQE DKDCPIKEEK GSPLNAAPYG

IESMSQDTEV RSRVVGGSLR GAQAASPAKG EPSLPEKDED

HALSYWKPFL VNMCVATVLT AGAYLCYRFL FNSNT.
```

In an embodiment, the agent that is an inhibitor of cancer cell invasion or metastasis restores interaction of PTP1b with epidermal growth factor receptor, insulin-like growth factor 1 receptor, colony stimulating factor 1 receptor, c-Src, Janus kinase 2, TYK2, focal adhesion kinase, STAT5, BCAR1, DOK1, beta-catenin, MET tyrosine kinase or cortactin. In an embodiment, the agent restores interaction of PTP1b with a protein listed in Table 1. In an embodiment, the agent restores the aforementioned interactions of PTP1b in the presence of Mena$^{INV}$.

Mena$^{INV}$ is an alternatively spliced variant of the Ena/VASP family protein Mena which includes the exon 3a. In an embodiment the Mena$^{INV}$ is human Mena$^{INV}$. Mena isoforms and agents for inhibiting mean isoforms are described in WO/2011/093989 and US 2010-0047240 A1, each of which are hereby incorporated by reference in their entirety. In an embodiment, the Mena$^{INV}$ is a mammalian Mena$^{INV}$. In an embodiment, the Mena$^{INV}$ is a human Mena$^{INV}$. In an embodiment, the Mena$^{INV}$ comprises the sequence AQSKVTATQD STNLRCIFC (SEQ ID NO:15). In an embodiment, the Mena$^{INV}$ is encoded by a nucleic acid comprising the sequence gcccagagca aggttactgc tacccaggac agcactaatt tgcgatgtat tttctgt (SEQ ID NO:16).

SHIP2 is also known as phosphatidylinositol-3,4,5-trisphosphate 5-phosphatase 2 (EC=3.1.3.86) and inositol polyphosphate phosphatase-like protein 1 (INPPL1). In an embodiment, the SHIP2 is a mammalian SHIP2. In an embodiment, the SHIP2 is a human SHIP2. In an embodiment, the SHIP2 comprises the sequence:

```
                                        (SEQ ID NO: 17)
MASACGAPGP GGALGSQAPS WYHRDLSRAA AEELLARAGR

DGSFLVRDSE SVAGAFALCV LYQKHVHTYR ILPDGEDFLA

VQTSQGVPVR RFQTLGELIG LYAQPNQGLV CALLLPVEGE

REPDPPDDRD ASDGEDEKPP LPPRSGSTSI SAPTGPSSPL

PAPETPTAPA AESAPNGLST VSHDYLKGSY GLDLEAVRGG

ASHLPHLTRT LATSCRRLHS EVDKVLSGLE ILSKVFDQQS

SPMVTRLLQQ QNLPQTGEQE LESLVLKLSV LKDFLSGIQK

KALKALQDMS STAPPAPQPS TRKAKTIPVQ AFEVKLDVTL

GDLTKIGKSQ KFTLSVDVEG GRLVLLRRQR DSQEDWTTFT

HDRIRQLIKS QRVQNKLGVV FEKEKDRTQR KDFIFVSARK

REAFCQLLQL MKNKHSKQDE PDMISVFIGT WNMGSVPPPK

NVTSWFTSKG LGKTLDEVTV TIPHDIYVFG TQENSVGDRE

WLDLLRGGLK ELTDLDYRPI AMQSLWNIKV AVLVKPEHEN

RISHVSTSSV KTGIANTLGN KGAVGVSFMF NGTSFGFVNC

HLTSGNEKTA RRNQNYLDIL RLLSLGDRQL NAFDISLRFT

HLFWFGDLNY RLDMDIQEIL NYISRKEFEP LLRVDQLNLE

REKHKVFLRF SEEEISFPPT YRYERGSRDT YAWHKQKPTG

VRTNVPSWCD RILWKSYPET HIICNSYGCT DDIVTSDHSP

VFGTFEVGVT SQFISKKGLS KTSDQAYIEF ESIEAIVKTA

SRTKFFIEFY STCLEEYKKS FENDAQSSDN INFLKVQWSS

RQLPTLKPIL ADIEYLQDQH LLLTVKSMDG YESYGECVVA

LKSMIGSTAQ QFLTFLSHRG EETGNIRGSM KVRVPTERLG

TRERLYEWIS IDKDEAGAKS KAPSVSRGSQ EPRSGSRKPA

FTEASCPLSR LFEEPEKPPP TGRPPAPPRA APREEPLTPR

LKPEGAPEPE GVAAPPPKNS FNNPAYYVLE GVPHQLLPPE

PPSPARAPVP SATKNKVAIT VPAPQLGHHR HPRVGEGSSS

DEESGGTLPP PDFPPPPLPD SAIFLPPSLD PLPGPVVRGR

GGAEARGPPP PKAHPRPPLP PGPSPASTFL GEVASGDDRS
```

```
CSVLQMAKTL SEVDYAPAGP ARSALLPGPL ELQPPRGLPS

DYGRPLSFPP PRIRESIQED LAEEAPCLQG GRASGLGEAG

MSAWLRAIGL ERYEEGLVHN GWDDLEFLSD ITEEDLEEAG

VQDPAHKRLL LDTLQLSK
```

As used herein, an "association" of a first molecular entity with a second is a physical association, such as binding or molecular interaction, of the first molecular entity with the second.

As used herein, a "predetermined control amount" is a value decided as a reference point to distinguish normal from afflicted. The concept of a control is well-established in the field, and can be determined, in a non-limiting example, empirically from non-afflicted subjects (versus afflicted subjects), and may be normalized as desired to negate the effect of one or more variables.

As used herein, an "inhibitor" of metastasis means an agent that attenuates, reduces or prevents one or more symptoms or one or more other parameters by which metastasis is characterized. Non-limiting examples of such parameters include uncontrolled degradation of the basement membrane and proximal extracellular matrix, and travel of tumor cells through the bloodstream or lymphatics, invasion, dysregulated adhesion, and proliferation at a secondary site. In an embodiment, the metastasis is of a primary tumor.

As used herein, "inhibitor" of invasion of a cancer cell means an agent that attenuates, reduces or prevents one or more symptoms of the progression of the cancer, such as spread to a site immediately adjacent to the origin site of the cancer.

In an embodiment, the Mena$^{INV}$ is inhibited through RNAi, for example by an siRNA or an shRNA. An siRNA (small interfering RNA) as used in the methods or compositions described herein comprises a portion which is complementary to an mRNA sequence encoding a mammalian Mena$^{INV}$, and the siRNA is effective to inhibit expression of mammalian Mena$^{INV}$. In an embodiment, the siRNA comprises a double-stranded portion (duplex). In an embodiment, the siRNA is 20-25 nucleotides in length. In an embodiment the siRNA comprises a 19-21 core RNA duplex with a one or 2 nucleotide 3' overhang on, independently, either one or both strands. The siRNA can be 5' phosphorylated or not and may be modified with any of the known modifications in the art to improve efficacy and/or resistance to nuclease degradation. In an embodiment the siRNA can be administered such that it is transfected into one or more cells.

In one embodiment, a siRNA of the invention comprises a double-stranded RNA wherein one strand of the double-stranded RNA is 80, 85, 90, 95 or 100% complementary to a portion of an RNA transcript of a gene encoding mammalian Mena$^{INV}$. In another embodiment, a siRNA of the invention comprises a double-stranded RNA wherein one strand of the RNA comprises a portion having a sequence the same as a portion of 18-25 consecutive nucleotides of an RNA transcript of a gene encoding mammalian Mena$^{INV}$. In yet another embodiment, a siRNA of the invention comprises a double-stranded RNA wherein both strands of RNA are connected by a non-nucleotide linker. Alternately, a siRNA of the invention comprises a double-stranded RNA wherein both strands of RNA are connected by a nucleotide linker, such as a loop or stem loop structure.

In one embodiment, a single strand component of a siRNA of the invention is from 14 to 50 nucleotides in length. In another embodiment, a single strand component of a siRNA of the invention is 14, 15, 16, 17, 18, 19, 20, 21, 22, 23, 24, 25, 26, 27, or 28 nucleotides in length. In yet another embodiment, a single strand component of a siRNA of the invention is 21 nucleotides in length. In yet another embodiment, a single strand component of a siRNA of the invention is 22 nucleotides in length. In yet another embodiment, a single strand component of a siRNA of the invention is 23 nucleotides in length. In one embodiment, a siRNA of the invention is from 28 to 56 nucleotides in length. In another embodiment, a siRNA of the invention is 40, 41, 42, 43, 44, 45, 46, 47, 48, 49, 50, 51, or 52 nucleotides in length. In yet another embodiment, a siRNA of the invention is 46 nucleotides in length.

In another embodiment, an siRNA of the invention comprises at least one 2'-sugar modification. In another embodiment, an siRNA of the invention comprises at least one nucleic acid base modification. In another embodiment, an siRNA of the invention comprises at least one phosphate backbone modification.

In one embodiment, RNAi inhibition of Mena$^{INV}$ is effected by a short hairpin RNA ("shRNA"). The shRNA can be introduced into the cell by transduction with a vector. In an embodiment, the vector is a lentiviral vector. In an embodiment, the vector comprises a promoter. In an embodiment, the promoter is a U6 or H1 promoter. In an embodiment the shRNA encoded by the vector is a first nucleotide sequence ranging from 19-29 nucleotides complementary to the target gene, or mRNA, in the present case encoding Mena$^{INV}$. In an embodiment the shRNA encoded by the vector also comprises a short spacer of 4-15 nucleotides (a loop, which does not hybridize) and a 19-29 nucleotide sequence that is a reverse complement of the first nucleotide sequence. In an embodiment the siRNA resulting from intracellular processing of the shRNA has overhangs of 1 or 2 nucleotides. In an embodiment the siRNA resulting from intracellular processing of the shRNA overhangs has two 3' overhangs. In an embodiment the overhangs are UU.

As used herein, the term "antibody" refers to an intact antibody, i.e. with complete Fc and Fv regions. "Fragment" refers to any portion of an antibody, or portions of an antibody linked together, such as, in non-limiting examples, a Fab, F(ab)$_2$, a single-chain Fv (scFv), which is less than the whole antibody but which is an antigen-binding portion and which competes with the intact antibody of which it is a fragment for specific binding. As such, a fragment can be prepared, for example, by cleaving an intact antibody or by recombinant means (e.g., an scFv generated by expressing the scFv in a host system and recovering it). See generally, Fundamental Immunology, Ch. 7 (Paul, W., ed., 2nd ed. Raven Press, N.Y. (1989), hereby incorporated by reference in its entirety). Antigen-binding fragments may be produced by recombinant DNA techniques or by enzymatic or chemical cleavage of intact antibodies or by molecular biology techniques. In some embodiments, a fragment is an Fab, Fab', F(ab')$_2$, F$_d$, F$_v$, complementarity determining region (CDR) fragment, single-chain antibody (scFv), (a variable domain light chain (V$_L$) and a variable domain heavy chain (V$_H$) linked via a peptide linker. In an embodiment the linker of the scFv is 10-25 amino acids in length. In an embodiment the peptide linker comprises glycine, serine and/or threonine residues. For example, see Bird et al., Science, 242: 423-426 (1988) and Huston et al., Proc. Natl. Acad. Sci. USA, 85:5879-5883 (1988) each of which are hereby incorporated by reference in their entirety), or a polypeptide that contains at least a portion of an antibody that is sufficient to confer Mena$^{INV}$-specific antigen binding on the polypeptide, including a diabody. From N-terminus to C-terminus, both the mature light and heavy chain variable domains comprise the regions FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md. (1987 and 1991)), Chothia & Lesk, J. Mol. Biol. 196:901-917 (1987), or Chothia et al., Nature 342: 878-883 (1989), each of which are hereby incorporated by reference in their entirety). As used herein, the term "polypeptide" encompasses native or artificial proteins, protein fragments and polypeptide analogs of a protein sequence. A polypeptide may be monomeric or polymeric. As used herein, an $F_d$ fragment means an antibody fragment that consists of the $V_H$ and CH1 domains; an $F_v$ fragment consists of the $V_L$ and $V_H$ domains of a single arm of an antibody; and a dAb fragment (Ward et al., Nature 341:544-546 (1989) hereby incorporated by reference in its entirety) consists of a $V_H$ domain. In some embodiments, fragments are at least 5, 6, 8 or 10 amino acids long. In other embodiments, the fragments are at least 14, at least 20, at least 50, or at least 70, 80, 90, 100, 150 or 200 amino acids long.

Antibodies of the invention can be monoclonal. The term "monoclonal antibody" is not intended, unless otherwise indicated, to be limited as regards to the source of the antibody or the manner in which it is made (e.g., by hybridoma, phage selection, recombinant expression, transgenic animals, etc.). The term "monoclonal antibody" as used herein refers to an antibody member of a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target Mena$^{INV}$, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins. Thus an identified monoclonal antibody can be produced by non-hybridoma techniques, e.g. by appropriate recombinant means once the sequence thereof is identified.

Antibodies of the invention can be isolated antibodies. As used herein, the terms "isolated antibody" refers to an antibody that by virtue of its origin or source of derivation has one to four of the following: (1) is not associated with naturally associated components that accompany it in its native state, (2) is free of other proteins from the same species, (3) is expressed by a cell from a different species, or (4) does not occur in nature.

In an embodiment the composition or pharmaceutical composition comprising one or more of the antibodies or fragments described herein is substantially pure with regard to the antibody or fragment. A composition or pharmaceutical composition comprising one or more of the antibodies or fragments described herein is "substantially pure" with regard to the antibody or fragment when at least about 60 to 75% of a sample of the composition or pharmaceutical composition exhibits a single species of the antibody or fragment. A substantially pure composition or pharmaceutical composition comprising one or more of the antibodies or fragments described herein can comprise, in the portion thereof which is the antibody or fragment, 60%, 70%, 80% or 90% of the antibody or fragment of the single species, more usually about 95%, and preferably over 99%. Antibody purity or homogeneity may tested by a number of means well known in the art, such as polyacrylamide gel electrophoresis or HPLC.

Antibodies of the invention can be human antibodies. As used herein, a "human antibody" unless otherwise indicated is one whose sequences correspond to (i.e. are identical in sequence to) an antibody that could be produced by a human and/or has been made using any of the techniques for making human antibodies as disclosed herein, but not one which has been made in a human. This definition of a human antibody specifically excludes a humanized antibody. A "human antibody" as used herein can be produced using various techniques known in the art, including phage-display libraries (e.g. Hoogenboom and Winter, J. Mol. Biol., 227:381 (1991); Marks et al., J. Mol. Biol., 222:581 (1991), hereby incorporated by reference in its entirety), by methods described in Cole et al., Monoclonal Antibodies and Cancer Therapy, Alan R. Liss, p. 77 (1985) (hereby incorporated by reference in its entirety); Boerner et al., J. Immunol., 147 (1):86-95 (1991) (hereby incorporated by reference in its entirety), van Dijk and van de Winkel, Curr. Opin. Pharmacol., 5: 368-74 (2001) (hereby incorporated by reference in its entirety), and by administering the antigen (e.g. Mena$^{INV}$) to a transgenic animal that has been modified to produce such antibodies in response to antigenic challenge, but whose endogenous loci have been disabled, e.g., immunized xenomice (see, e.g., U.S. Pat. Nos. 5,939,598; 6,075,181; 6,114,598; 6,150,584 and 6,162,963 to Kucherlapati et al. regarding XENOMOUSE™ technology, each of which patents are hereby incorporated by reference in their entirety), e.g. VelocImmune® (Regeneron, Tarrytown, N.Y.), e.g. UltiMab® platform (Medarex, now Bristol Myers Squibb, Princeton, N.J.). See also, for example, Li et al., Proc. Natl. Acad. Sci. USA, 103:3557-3562 (2006) regarding human antibodies generated via a human B-cell hybridoma technology. See also KM Mouse® system, described in PCT Publication WO 02/43478 by Ishida et al., in which the mouse carries a human heavy chain transchromosome and a human light chain transgene, and the TC mouse system, described in Tomizuka et al. (2000) Proc. Natl. Acad. Sci. USA 97:722-727, in which the mouse carries both a human heavy chain transchromosome and a human light chain transchromosome, both of which are hereby incorporated by reference in their entirety. In each of these systems, the transgenes and/or transchromosomes carried by the mice comprise human immunoglobulin variable and constant region sequences.

The term "human antibody", as used herein, is intended to include antibodies having variable regions in which both the framework and CDR regions are sequences of human origin or identical thereto other than antibodies naturally occurring in a human or made in a human. Furthermore, if the antibody (e.g. an intact antibody rather than, for example, an Fab fragment) contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. In one non-limiting embodiment, where the human antibodies are human monoclonal antibodies, such antibodies can be produced by a hybridoma which includes a B cell obtained from a transgenic nonhuman animal, e.g., a transgenic mouse, having a genome comprising a human heavy chain transgene and a light chain transgene fused to an immortalized cell.

Antibodies of the invention can be recombinant human antibodies. The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Antibodies of the invention can be humanized antibodies. "Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region (HVR) of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin variable domain are replaced by corresponding non-human residues. These modifications may be made to further refine antibody performance. Furthermore, in a specific embodiment, humanized antibodies may comprise residues that are not found in the recipient antibody or in the donor antibody. In an embodiment, the humanized antibodies do not comprise residues that are not found in the recipient antibody or in the donor antibody. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. See, e.g., Jones et al., Nature 321:522-525 (1986); Riechmann et al., Nature 332:323-329 (1988); Presta, Curr. Op. Struct. Biol. 2:593-596 (1992); Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409, the contents of each of which references and patents are hereby incorporated by reference in their entirety. In one embodiment where the humanized antibodies do comprise residues that are not found in the recipient antibody or in the donor antibody, the Fc regions of the antibodies are modified as described in WO 99/58572, the content of which is hereby incorporated by reference in its entirety.

Techniques to humanize a monoclonal antibody are described in U.S. Pat. Nos. 4,816,567; 5,807,715; 5,866,692; 6,331,415; 5,530,101; 5,693,761; 5,693,762; 5,585,089; and 6,180,370, the content of each of which is hereby incorporated by reference in its entirety.

A number of "humanized" antibody molecules comprising an antigen-binding site derived from a non-human immunoglobulin have been described, including antibodies having rodent or modified rodent V regions and their associated complementarity determining regions (CDRs) fused to human constant domains. See, for example, Winter et al. Nature 349: 293-299 (1991), Lobuglio et al. Proc. Nat. Acad. Sci. USA 86: 4220-4224 (1989), Shaw et al. J. Immunol. 138: 4534-4538 (1987), and Brown et al. Cancer Res. 47: 3577-3583 (1987), the content of each of which is hereby incorporated by reference in its entirety. Other references describe rodent hypervariable regions or CDRs grafted into a human supporting framework region (FR) prior to fusion with an appropriate human antibody constant domain. See, for example, Riechmann et al. Nature 332: 323-327 (1988), Verhoeyen et al. Science 239: 1534-1536 (1988), and Jones et al. Nature 321: 522-525 (1986), the content of each of which is hereby incorporated by reference in its entirety. Another reference describes rodent CDRs supported by recombinantly veneered rodent framework regions—European Patent Publication No. 0519596 (incorporated by reference in its entirety). These "humanized" molecules are designed to minimize unwanted immunological response toward rodent anti-human antibody molecules which limits the duration and effectiveness of therapeutic applications of those moieties in human recipients. The antibody constant region can be engineered such that it is immunologically inert (e.g., does not trigger complement lysis). See, e.g. PCT Publication No. WO99/58572; UK Patent Application No. 9809951.8. Other methods of humanizing antibodies that may also be utilized are disclosed by Daugherty et al., Nucl. Acids Res. 19: 2471-2476 (1991) and in U.S. Pat. Nos. 6,180,377; 6,054,297; 5,997,867; 5,866,692; 6,210,671; and 6,350,861; and in PCT Publication No. WO 01/27160 (each incorporated by reference in their entirety).

Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

In embodiments, the antibodies or fragments herein can be produced recombinantly, for example antibodies expressed using a recombinant expression vector transfected into a host cell, antibodies isolated from a recombinant, combinatorial human antibody library, antibodies isolated from an animal (e.g., a mouse) that is transgenic for human immunoglobulin genes.

The antibody or fragment may specifically bind to the Mena$^{INV}$. As used herein, the terms "is capable of specifically binding", "specifically binds", or "preferentially binds" refers to the property of an antibody or fragment of binding to the (specified) antigen with a dissociation constant that is <1 µM, preferably <1 nM and most preferably <10 pM. In an embodiment, the Kd of the antibody for Mena$^{INV}$ is 250-500 pM. An epitope that "specifically binds", or "preferentially binds" (used interchangeably herein) to an antibody or a polypeptide is a term well understood in the art, and methods to determine such specific or preferential binding are also well known in the art. A molecular entity is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a Mena$^{INV}$ conformational epitope is an antibody that binds this epitope with greater affinity, avidity, more readily, and/or with greater duration than it binds to other Mena$^{INV}$ epitopes or non-Mena$^{INV}$ epitopes or to Mena. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding.

Depending on the amino acid sequences of the constant domains of their heavy chains, antibodies (immunoglobulins) can be assigned to different classes. The antibody or fragment can be, e.g., any of an IgG, IgD, IgE, IgA or IgM antibody or fragment thereof, respectively. In an embodiment the antibody is an immunoglobulin G. In an embodiment the antibody fragment is a fragment of an immunoglobulin G. In an embodiment the antibody is an IgG1, IgG2, IgG2a, IgG2b, IgG3 or IgG4. In an embodiment the antibody comprises sequences from a human IgG1, human IgG2, human IgG2a, human IgG2b, human IgG3 or human IgG4. A combination of any of these antibodies subtypes can also be used. One consideration in selecting the type of antibody to be used is the desired serum half-life of the antibody. For example, an IgG generally has a serum half-life of 23 days, IgA 6 days, IgM 5 days, IgD 3 days, and IgE 2 days. (Abbas A K, Lichtman A H, Pober J S. Cellular and Molecular Immunology, 4th edition, W.B. Saunders Co., Philadelphia, 2000, hereby incorporated by reference in its entirety).

In an embodiment the antibody or fragment neutralizes Mena$^{INV}$ when bound thereto.

The "variable region" or "variable domain" of an antibody refers to the amino-terminal domains of the heavy or light chain of the antibody. The variable domain of the heavy chain may be referred to as "V$_H$." The variable domain of the light chain may be referred to as "V$_L$." These domains are generally the most variable parts of an antibody and contain the antigen-binding sites. The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (4 based on the amino acid sequences of their constant domains. "Framework" or "FR" residues are those variable domain residues other than the HVR residues as herein defined.

The term "hypervariable region" or "HVR" when used herein refers to the regions of an antibody variable domain which are hypervariable in sequence and/or form structurally defined loops. Generally, antibodies comprise six HVRs; three in the V$_H$ (H1, H2, H3) and three in the V$_L$ (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996). A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991) hereby incorporated by reference in its entirety). Chothia refers instead to the location of the structural loops (Chothia and Lesk, J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. HVRs may comprise "extended HVRs" as follows: 24-36 or 24-34 (L1), 46-56 or 50-56 (L2) and 89-97 or 89-96 (L3) in the V$_L$ and 26-35 (H1), 50-65 or 49-65 (H2) and 93-102, 94-102, or 95-102 (H3) in the V$_H$. The variable domain residues are numbered according to Kabat et al., supra, for each of these definitions.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine of the Fc region may be removed, for example, during production or purification of the antibody, or by recombinantly engineering the nucleic acid encoding a heavy chain of the antibody. Accordingly, an intact antibody as used herein may be an antibody with or without the otherwise C-terminal cysteine.

Compositions or pharmaceutical compositions comprising the antibodies, ScFvs or fragments of antibodies disclosed herein are preferably comprise stabilizers to prevent loss of activity or structural integrity of the protein due to the effects of denaturation, oxidation or aggregation over a period of time during storage and transportation prior to use. The compositions or pharmaceutical compositions can comprise one or more of any combination of salts, surfactants, pH and tonicity agents such as sugars can contribute to overcoming aggregation problems. Where a composition or pharmaceutical composition of the present invention is used as an injection, it is desirable to have a pH value in an approximately neutral pH range, it is also advantageous to minimize surfactant levels to avoid bubbles in the formulation which are detrimental for injection into subjects. In an embodiment, the composition or pharmaceutical composition is in liquid form and stably supports high concentrations of bioactive antibody in solution and is suitable for parenteral administration, including intravenous, intramuscular, intraperitoneal, intradermal and/or subcutaneous injection. In an embodiment, the composition or pharmaceutical composition is in liquid form and has minimized risk of bubble formation and anaphylactoid side effects. In an embodiment, the composition or pharmaceutical composition is isotonic. In an embodiment, the composition or pharmaceutical composition has a pH or 6.8 to 7.4.

In an embodiment the ScFvs or fragments of antibodies disclosed herein are lyophilized and/or freeze dried and are reconstituted for use.

Examples of pharmaceutically acceptable carriers include, but are not limited to, phosphate buffered saline solution, sterile water (including water for injection USP), emulsions such as oil/water emulsion, and various types of wetting agents. Preferred diluents for aerosol or parenteral administration are phosphate buffered saline or normal (0.9%) saline, for example 0.9% sodium chloride solution, USP. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000, the content of each of which is hereby incorporated in its entirety). In non-limiting examples, the can comprise one or more of dibasic sodium phosphate, potassium chloride, monobasic potassium phosphate, polysorbate 80 (e.g. 2-[2-[3,5-bis(2-hydroxyethoxy) oxolan-2-yl]-2-(2-hydroxyethoxy)ethoxy]ethyl (E)-octadec-9-enoate), disodium edetate dehydrate, sucrose, monobasic sodium phosphate monohydrate, and dibasic sodium phosphate dihydrate.

The antibodies, or fragments of antibodies, or compositions, or pharmaceutical compositions described herein can also be lyophilized or provided in any suitable forms including, but not limited to, injectable solutions or inhalable solutions, gel forms and tablet forms.

The term "Kd", as used herein, is intended to refer to the dissociation constant of an antibody-antigen interaction. One way of determining the Kd or binding affinity of antibodies to $Mena^{INV}$ is by measuring binding affinity of monofunctional Fab fragments of the antibody. (The affinity constant is the inverted dissociation constant). To obtain monofunctional Fab fragments, an antibody (for example, IgG) can be cleaved with papain or expressed recombinantly. The affinity of an anti-$Mena^{INV}$ Fab fragment of an antibody can be determined by surface plasmon resonance (BIAcore3000™ surface plasmon resonance (SPR) system, BIAcore Inc., Piscataway N.J.). CM5 chips can be activated with N-ethyl-N'-(3-dimethylaminopropyl)-carbodiinide hydrochloride (EDC) and N-hydroxysuccinimide (NHS) according to the supplier's instructions. $Mena^{INV}$ can be diluted into 10 mM sodium acetate pH 4.0 and injected over the activated chip at a concentration of 0.005 mg/mL. Using variable flow time across the individual chip channels, two ranges of antigen density can be achieved: 100-200 response units (RU) for detailed kinetic studies and 500-600 RU for screening assays. Serial dilutions (0.1-10× estimated Kd) of purified Fab samples are injected for 1 min at 100 microliters/min and dissociation times of up to 2 h are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data to a 1:1 Langmuir binding model (Karlsson, R. Roos, H. Fagerstam, L. Petersson, B. (1994). Methods Enzymology 6. 99-110, the content of which is hereby incorporated in its entirety) using the BIA evaluation program. Equilibrium dissociation constant (Kd) values are calculated as $k_{off}/k_{on}$. This protocol is suitable for use in determining binding affinity of an antibody or fragment to any $Mena^{INV}$. Other protocols known in the art may also be used. For example, ELISA of $Mena^{INV}$ with mAb can be used to determine the kD values. The Kd values reported herein used this ELISA-based protocol.

In an embodiment of the methods and of the compositions herein, the $Mena^{INV}$ is a human $Mena^{INV}$. In an embodiment of the methods and of the compositions herein, the Mena is a human Mena. In an embodiment of the methods and of the compositions herein, the PTP1b is a human PTP1b. In an embodiment of the methods and of the compositions herein, the growth factor receptor is a human growth factor receptor.

As used herein a "small organic molecule" is an organic compound which contains carbon-carbon bonds, and has a molecular weight of less than 2000. The small molecule may be a substituted hydrocarbon or an substituted hydrocarbon. In an embodiment, the small molecule has a molecular weight of less than 1500. In an embodiment, the small molecule has a molecular weight of less than 1000.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group subjectly and all possible subgroups of the main group, but also the main group absent one or more of the group members. The present invention also envisages the explicit exclusion of one or more of any of the group members in the claimed invention.

"And/or" as used herein, for example, with option A and/or option B, encompasses the separate embodiments of (i) option A, (ii) option B, and (iii) option A plus option B.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

Experimental Details

Herein is disclosed a mechanism underlying increased carcinoma cell invasion due to the inclusion of exon 3a of the Ena/VASP family protein, Mena. The inclusion of exon 3a, resulting in the splice isoform Mena$^{INV}$, occurs normally during neuronal development and during pathological states, such as cancer [1, 2]. However, the expression of Mena$^{INV}$ mRNA is significantly upregulated in invasive tumor cells in vivo [1, 3, 4]. Disclosed herein is the role of Mena$^{INV}$-containing invasive tumor cell population in resistance to therapy and as a tool to stratify patients for different therapeutic interventions.

Applicants discovered that the protein tyrosine phosphatase PTP1b is dysregulated upon Mena$^{INV}$ expression. PTP1b contains a potential Mena-interacting site and exists within a constitutive complex with endogenous and ectopically expressed Mena (FIG. 1) Inhibition of PTP1b activity increases cell invasion and growth factor sensitivity in vitro and in vivo, similar to the behavior of tumor cells that express Mena$^{INV}$ (FIG. 2). Further, cells expressing Mena$^{INV}$ exhibit increased tyrosine phosphorylation of more than 30 proteins, many of which are known PTP1b targets (Table 1). This 'Mena$^{INV}$-signature' represents therapeutic targets specific for decreasing tumor cell invasion.

TABLE 1

Protein phosphorylation sites with increased phosphorylation of at least 20% in MDA-MB231 cells expressing Mena$^{INV}$ vs. GFP-vector control upon stimulation with 0.25 nM EGF for 60 sec. Phosphosites were identified by enrichment for tyrosine phosphorylated residues, followed by mass spectrometry.

| GI | Protein | Abrev/Site | Average Fold Change at 0.25 nM EGF |
|---|---|---|---|
| 22325381 | intersectin 2 isoform 3 | ITSN2 (Y968) | 2.68 |
| 20357552 | cortactin isoform a | CTTN (S418/Y421) | 2.65 |
| 46370071 | GRB2-associated binding protein 1 isoform a | GAB1 (Y627) | 2.25 |
| 44662836 | breast cancer anti-estrogen resistance 1 | p130CAS (Y287) | 2.17 |
| 63054864 | phosphoprotein associated with glycosphingolipid microdomains 1 | PAG1 (Y417) | 2.15 |
| 150417981 | Rho GTPase activating protein 35 | ARHGAP35 (Y1105) | 1.95 |
| 29725609 | epidermal growth factor receptor isoform a | EGFR (Y1148) = Y1172/3 | 1.83 |
| 148368962 | NKF3 kinase family member | PEAK1 | 1.83 |
| 32261324 | SHC (Src homology 2 domain containing) transforming protein 1 isoform p52Shc | SHC (Y427) | 1.75 |
| 29725609 | epidermal growth factor receptor isoform a | EGFR (Y1173) = Y1197 | 1.73 |
| 38201638 | homeodomain-interacting protein kinase 1 isoform 2 | HIPK1 (Y352) | 1.72 |
| 31543838 | tyrosine kinase 2 | TYK2 (Y292) | 1.68 |
| 4755142 | inositol polyphosphate phosphatase-like 1 | SHIP2 (Y886) | 1.65 |
| 63054864 | phosphoprotein associated with glycosphingolipid microdomains 1 | PAG1 (Y227) | 1.62 |
| 157909822 | pragmin | SGK223 (Y413) | 1.61 |
| 4757756 | annexin A2 isoform 2 | ANXA2 (Y30) | 1.56 |
| 51702526 | Wiskott-Aldrich syndrome gene-like protein | NWASP (Y256) | 1.54 |
| 106879210 | Src homology 2 domain containing adaptor protein B | SHB (Y246) | 1.53 |
| 4506903 | splicing factor, arginine/serine-rich 9 | SFSR9 | 1.51 |
| 63054864 | phosphoprotein associated with glycosphingolipid microdomains 1 | PAG1 (Y387) | 1.51 |
| 26986534 | Rho GTPase activating protein 12 | ARHGAP12 (Y243) | 1.50 |
| 12667788 | myosin, heavy polypeptide 9, non-muscle | MYH9(Y11) | 1.44 |
| 31377782 | protein kinase C, delta | PKCD (Y313) | 1.44 |
| 18765750 | dual-specificity tyrosine-(Y)-phosphorylation regulated kinase 1A isoform 3 | DYRK1A (Y145) | 1.41 |
| 66346708 | membrane associated guanylate kinase, WW and PDZ domain containing 1 isoform b | MAGI1 (Y373) | 1.41 |
| 41872583 | Rho-associated, coiled-coil containing protein kinase 2 | ROCK2 (Y722) | 1.40 |
| 21361831 | partitioning-defective protein 3 homolog | PARD3 (Y1080) | 1.40 |
| 4758302 | enhancer of rudimentary homolog | ERH (Y92) | 1.39 |
| 20986531 | mitogen-activated protein kinase 1 | ERK2 (T185/Y187) | 1.39 |
| 44662836 | breast cancer anti-estrogen resistance 1 | p130CAS (Y249) | 1.34 |
| 4506345 | paxillin | PXN (Y118) | 1.34 |
| 44662836 | breast cancer anti-estrogen resistance 1 | p130CAS (Y327) | 1.29 |
| 44662836 | breast cancer anti-estrogen resistance 1 | p130CAS (Y410) | 1.29 |
| 4757756 | annexin A2 isoform 2 [Homo sapiens] | ANXA2 (Y317/8/9) | 1.28 |

TABLE 1-continued

Protein phosphorylation sites with increased phosphorylation of at least 20% in MDA-MB231 cells expressing Mena$^{INV}$ vs. GFP-vector control upon stimulation with 0.25 nM EGF for 60 sec. Phosphosites were identified by enrichment for tyrosine phosphorylated residues, followed by mass spectrometry.

| GI | Protein | Abrev/Site | Average Fold Change at 0.25 nM EGF |
|---|---|---|---|
| 15451856 | caveolin 1 | CAV1 (Y14) | 1.28 |
| 32967311 | ephrin receptor EphA2 | EPHA2 (Y575) | 1.28 |
| 68989256 | ras inhibitor RIN1 | RIN 1 (Y36) | 1.28 |
| 91718897 | mitogen-activated protein kinase 3 isoform 2 | ERK1 (Y204) | 1.26 |
| 4505409 | non-metastatic cells 1, protein (NM23A) expressed in isoform b | NME2 (Y52) | 1.26 |
| 106879210 | Src homology 2 domain containing adaptor protein B | SHB (Y268) | 1.25 |
| 153792590 | heat shock protein 90kDa alpha (cytosolic), class A member 1 isoform 1 | HSP90A (Y284) | 1.24 |
| 38201675 | syndecan 4 precursor | SDC4 (Y197) | 1.24 |
| 42518065 | tight junction protein 2 (zona occludens 2) isoform 2 | ZO2 (Y1118) | 1.22 |
| 21361340 | glycogen synthase kinase 3 alpha | GSK3 (Y216) | 1.20 |

A proximity ligation association assay (PLA) approach was used to quantify the interaction of EGFR with PTP1b in the presence of endogenous Mena or ectopic Mena and Mena$^{INV}$ (FIG. 3). PLA is an immunodetection technique that indicates when protein targets are within 40 nm of one another [5]. It is understood EGFR and PTP1b will be within the PLA limit of detection while PTP1b dephosphorylates EGFR, a known substrate of PTP1b [6]. It was found that expression of Mena$^{INV}$ decreases EGFR-PTP1b interaction upon EGF stimulation. Further, the inhibition of PTP1b in MDA-MB231 cells increases EGFR phosphorylation on Y1173 to levels exhibited by MDA-MB231 cells expressing Mena$^{INV}$. These data show that decreased interaction between PTP1b and EGFR is important in driving the Mena$^{INV}$-induced increased in invasion. Accordingly, an assay can be employed to screen small molecules, protein biologics, and short hairpin RNA sequences etc. for the ability to rescue the EGFR-PTP1b interaction in cells expressing Mena$^{INV}$.

Figure 4:
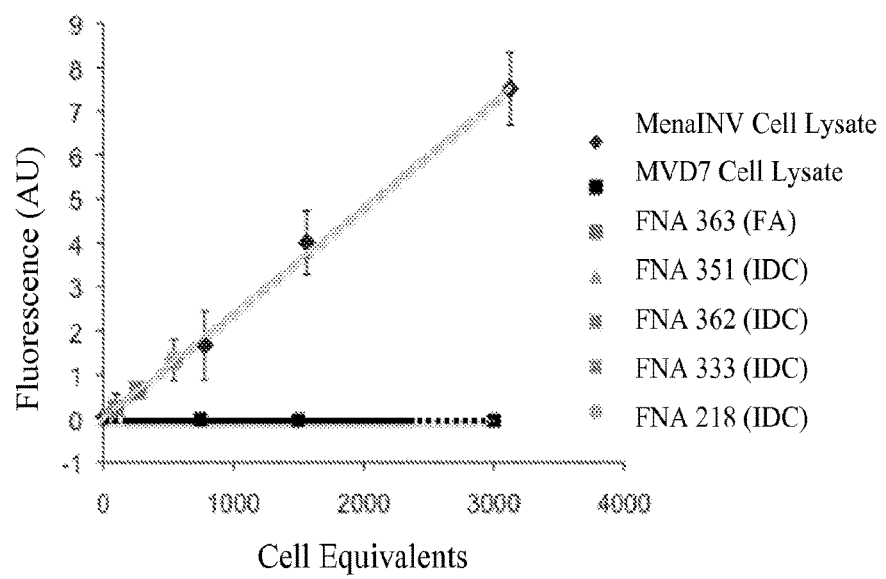
FIG. 4: Example of Mena$^{INV}$ capture ELISA using human fine needle aspirate samples from breast carcinoma patients. MDA-MB231 GFP-Mena$^{INV}$ or MVD7 (Ena/VASP null) cells were serially diluted and lysed to determine 1) signal sensitivity and 2) signal specificity in an ELISA using the Mena$^{INV}$ antibody for capture. IDC=invasive ductal carcinoma, FA=fibroadenoma. Note that no Mena$^{INV}$ was measured in the FA sample. Error bars represent the range of signal in duplicate samples. Mena$^{INV}$ antibody clone 48-1 was used as capture antibody at 1:2000.

In parallel, an ELISA-based assay was developed for identification of Mena$^{INV}$ in cell lysate (FIG. 4). This assay can be employed to quantitatively determine changes in Mena$^{INV}$ expression in cells before, during and after drug treatment. The Mena$^{INV}$ ELISA can also be employed in the clinic to stratify patients, thus determining the appropriate therapeutic regime given the absolute level of Mena$^{INV}$ within, for example, a biopsy or fine need aspirate sample. In an initial study (FIG. 4), Mena$^{INV}$ was successfully measured using fine needle aspirate-derived lysates of invasive ductal carcinoma, but not in lysate from a patient presenting with a fibroadenoma (non-tumor sample).

Supporting Experiments

Figures 5A, 5B:
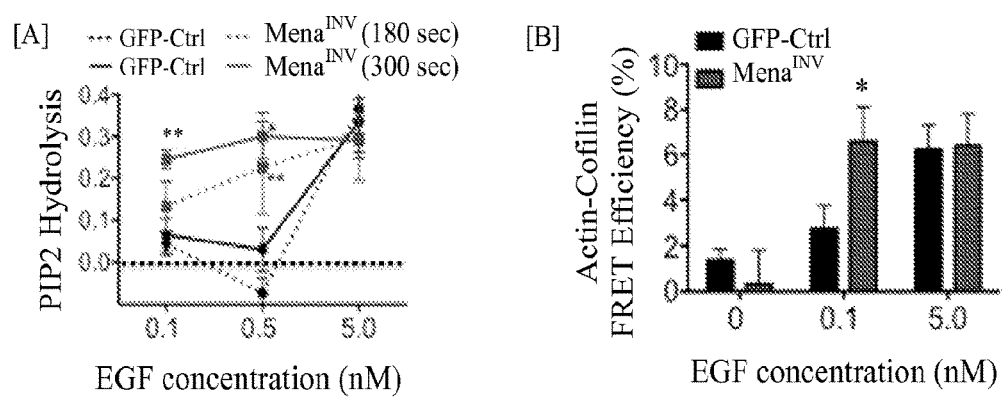
FIG. 5A-5B: Increased EGFR activation is propagated through the intracellular signaling pathway leading to actin polymerization. MTLn3 cells were transiently transfected with a mCherry-tagged PH-domain biosensor targeting PI(4,5)P2, starved in L15 media and then stimulated with the indicated concentrations of EGF. The decrease in mCherry signal (as a fraction of the total signal at t=0 sec) is shown in (A) and indicates that PLCγ activity is greater in Mena$^{INV}$ versus GFP-control cells after stimulation with 0.1 and 0.5 nM EGF. Hydrolysis of PIP2 (A) redistributes cofilin, allowing for actin severing and the formation of polymerization-competent actin barbed ends. The level of actin-cofilin association is also greater in Mena$^{INV}$ versus GFP-control cells (B), suggesting that the increased EGFR pathway activation is responsible for the increased membrane protrusion exhibited by cells expression Mena$^{INV}$. *p<0.05, **p<0.01 using a ANOVA with Tukey post-processing test.

Whether the increase in EGFR activation could account for the increased actin polymerization-driven membrane protrusion in cells expressing Mena$^{INV}$ or Mena$^{INV+}$ was investigated. One route to actin polymerization downstream of the EGF receptor involves activation of PLCγ that leads to hydrolysis of membrane bound PI(4,5)P2 and relocalization of actin binding proteins, including cofilin, an actin severing protein that is required to generate free barbed F-actin ends to initiate actin polymerization during EGF-elicited lamellipodial protrusion in carcinoma cells. Using MTLn3 adenocarcinoma cells, a well-characterized PH-domain probe for PLC activation was employed, PH-PLCδ1, to investigate the dynamics of PIP2 hydrolysis at EGF concentrations shown to elicit differential membrane protrusion responses. PIP2 hydrolysis was significantly increased in GFP-Mena$^{INV}$ cells at 180 and 300 sec post-EGF stimulation versus those expressing an GFP-control plasmid at 0.1 and 0.5 nM EGF (FIG. 5A,B).

To determine if increased PLCγ activity in Mena$^{INV}$-expressing cells elevated actin severing activity, the association of cofilin with filmentous actin using donor-acceptor FRET was measured. In this end-point assay, an increase in FRET efficiency is indicative of cofilin-actin interaction that serves as a surrogate measurement for the amount of cofilin-actin severing activity. MTLn3 cells expressing Mena$^{INV}$ exhibited increased cofilin-actin FRET efficiency at very low concentrations of EGF (0.1 nM, FIG. 5C). Taken together, the increase in PIP2 hydrolysis concomitant with increased cofilin-actin interaction, indicate that the hyperactivation of EGFR at low growth factor concentrations in cells expressing Mena$^{INV}$ contributes to the observed increase in actin polymerization-driven lamellipodial protrusion.

Interestingly, it was found that although expression of the + exon (an additional 246 amino acids included in the proline-rich region and containing several predicted SH3-binding sites) causes significant morphological changes in fibroblasts, it confers little additional affect on breast cancer cell invasion when expressed in concert with the short INV exon. These data indicate that it is the inclusion of the INV exon that drives increased actin polymerization and invasive behavior in breast cancer cells.

Figures 6A, 6B, 6C, 6D:
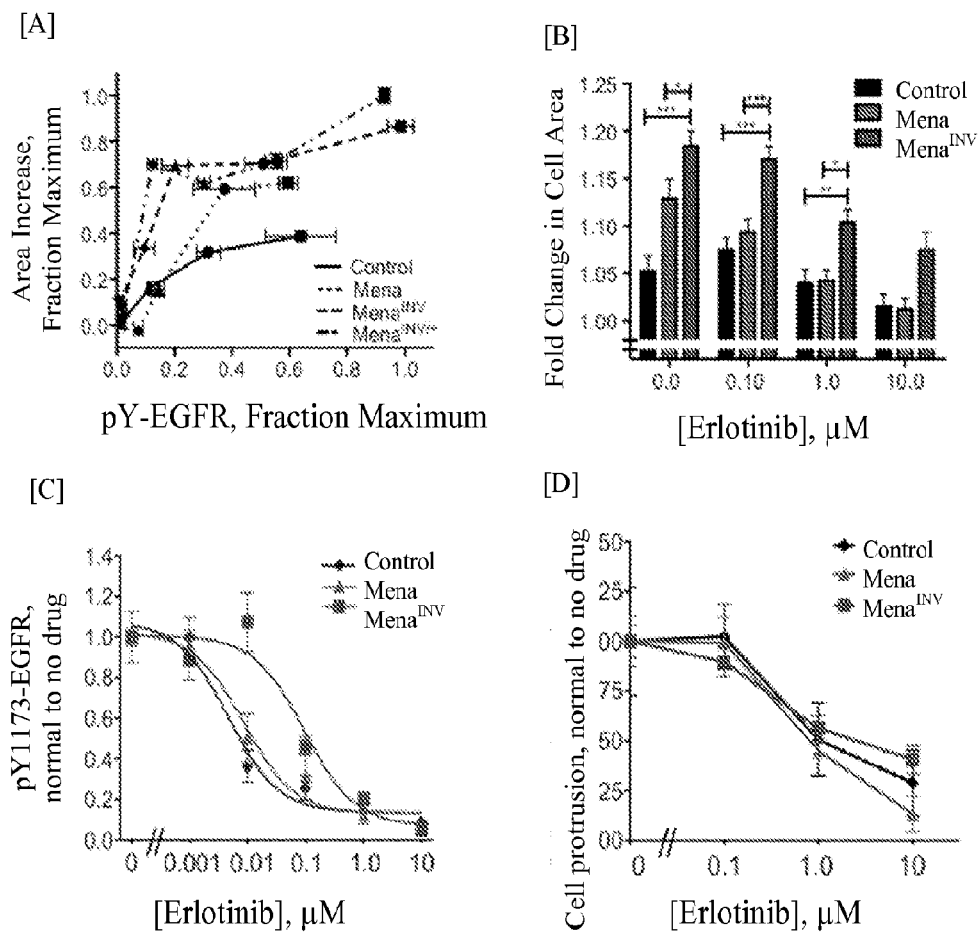
FIG. 6A-6C: Cells expressing Mena$^{INV}$ are resistant to EGFR targeted kinase inhibitors. [A] Examination of membrane protrusion as a function of EGFR phosphorylation suggests that targeted inhibition of EGFR will not decrease actin polymerization in cells that express the Mena invasive isoforms. Data was combined to generate novel hypothesis regarding clinically-relevant treatment regimes for invasive breast cancer. [B] Significantly higher doses of erlotinib (Tarceva®) are required to decrease membrane protrusion in cells expressing Mena$^{INV}$. Cells were serum starved for 4 hrs and then stimulated with 1 nM EGF in the presence of increasing doses of erlotinib. Membrane protrusion was quantified 8 min post-EGF/drug addition. *p<0.05, p<0.01, *p<0.001. Concomitant with increased membrane protrusion, cells expressing the Mena invasive isoforms are also resistant to erlotinib [C] in regards to EGFR phosphorylation. Cells were serum starved and then stimulated with EGF and drug for 3 min. Cells were lysed and the level of EGFR-pY1173 was determined by semi-quantitative Western Blot. Normalizing the protrusion response to the no-drug control of each cell line illustrates a common response across cell lines suggesting that the receptor is accessible to drug binding.
Figures 7A, 7B, 7C, 7D:
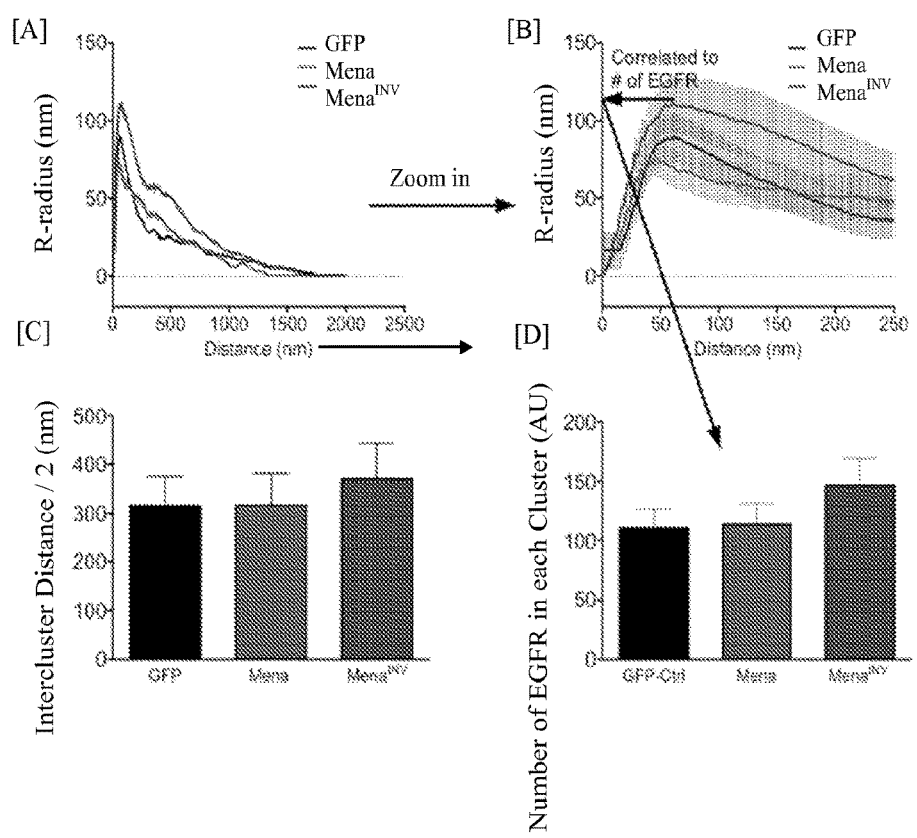
FIG. 7A-7D: Ectopic expression of Mena or Mena$^{INV}$ does not significantly affect EGFR clustering. MDA-MB231 cells were plated on 100 µg/mL collagen I overlayed with 0.2% matrigel and fixed for electron microscopic analysis. A monoclonal antibody to the extracellular domain of EGFR (mAb 225) was utilized along with ultra-small gold particles to analyze the distribution of EGFR along the lamellipodia of the cells. Ripley's K-analysis (A, B) was employed to determine the EGFR intercluster distance (C) and the relative number of EGFR per cluster (D). At least 40 cells were analyzed per condition. There were no significant differences in either parameter (C, D) suggesting that EGFR membrane presentation is normal in cells with ectopic Mena or Mena$^{INV}$ expression.

Erlotinib (Tarceva®), a clinically-utilized therapeutic that inhibits EGFR kinase activity, abrogates in vivo invasion of GFP-expressing mammary carcinoma cells, but does not fully block invasion of cells that express Mena$^{INV}$. To determine whether the enhanced EGF sensitivity of Mena$^{INV}$-expressing cells contributes to the decrease in efficacy of EGFR-targeted therapeutics during cell invasion, the amount of EGFR activation required for lamellipodial protrusion in cells expressing GFP, GFP-Mena, GFP-Mena$^{INV}$, and GFP-Mena$^{INV}$+ was compared by combining the data. This analysis illustrates that only a small fraction of maximal EGFR phosphorylation is required for robust actin polymerization activity in cells expressing Mena$^{INV}$. Considering that it is pharmacologically difficult to obtain complete inhibition of kinase activity in vivo, the low level of EGFR activation required for membrane protrusion in Mena$^{INV}$-expressing cells could allow the cells with the highest metastatic potential to subvert therapeutic intervention. To test this hypothesis, serum-starved cells were treated with 1.0 nM EGF and increasing doses of DMSO (carrier control) or erlotinib and measured EGFR phosphorylation at 3 min post-stimulation (FIG. 6B). Cells expressing Mena$^{INV}$ were significantly less sensitive to erlotinib, requiring ten-fold more drug to decrease receptor activation compared to controls (FIG. 6B). Equivalent results were obtained with gefitnib, another EGFR-targeted therapeutic with a similar mechanism of action. Based upon the quantitative analysis shown in FIG. 6A, it was hypothesized that actin polymerization would not be effectively abrogated in cells expressing Mena$^{INV}$ unless at least 1 µM erlotinib was co-dosed with growth factor. Similarly, ten-fold more erlotinib was required to decrease lamellipodial protrusion significantly in Mena$^{INV}$-expressing cells compared to cells expressing control GFP or Mena (FIG. 6C). It was asked if differential drug binding might underlie the measured response, but upon normalizing cell protrusion to the no-drug protrusion response within each cell line the efficacy of the drug was roughly equivalent (FIG. 6D) suggesting that erlotinib binding is independent of Mena$^{INV}$ expression. Further, electron microscopy was performed using ultra-small gold particles to examine receptor distribution along the cell membrane to determine if increased clustering of the receptor might affect drug binding or signal propagation. However, no significant difference was found in receptor clustering in the analysis (FIG. 7). Together, these data show that the Mena$^{INV}$ positive carcinoma cells are less refractory to EGFR inhibition in vivo due to the increased signaling flux initiated by increased EGF sensitivity at the receptor level.

Figure 8A:
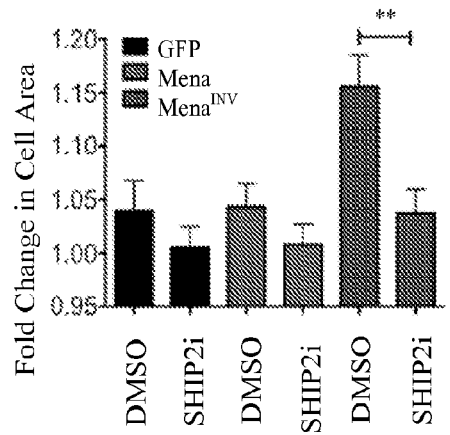
FIG. 8A-8D: The activity of SHIP2 is not required for early stages of Mena$^{INV}$-induced lamellipodial protrusion. MDA-MB231 (A,B) and MTLn3 (C,D) cells were incubated for 4 h with 10 µM AS1949490 in serum-free medium. Cells were stimulated with 0.25 nM (A,B) or 0.5 nM (C,D) EGF and membrane protrusion was recorded 8 min. The addition of AS1949490 decreased membrane protrusion to GFPcontrol levels at 8 min post-EGF stimulation (A,C), but the initial protrusion response of Mena$^{INV}$ expressing cells was not effected (B,D).
Figure 8B:
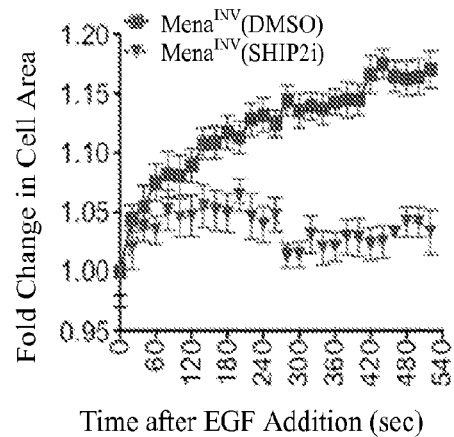
Figure 8C:
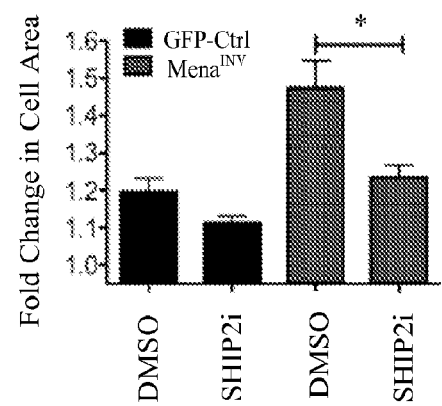
Figure 8D:
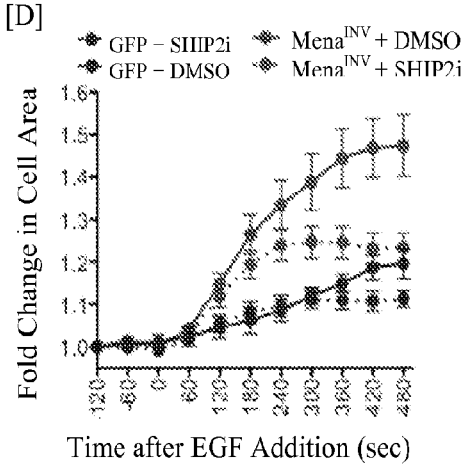

What could account for the phenotypes associated with inclusion of the INV exon of Mena, that include: increased activation of EGFR and downstream EGFR-mediated, motility-specific signaling pathways, increased cell invasion, and decreased efficacy of tyrosine kinase inhibition? One route to aberrant signal amplification is dysregulation of control nodes within the protein network, such as phosphatases, that could lead to prolonged or amplified phosphorylation states. Identification of potential Mena and Mena$^{INV}$ interacting partners that might affect phosphatase activity can shed light on this. Attempts were made at identification of Mena isoforms-specific interacting partners via mass spectrometric analysis. Several unsuccessful attempts to purify Mena interacting partners through a co-immunprecipitation and the mass spectrometric approach resulted. A bioinformatics screening approach was then used. A list of 38 human phosphatases was queried for potential Ena/VASP interaction motifs, with the hypothesis that an interaction between Mena$^{INV}$ and a phosphatase important for attenuating growth factor responses could lead to increased signaling upon growth factor stimulation. Three human phosphatases that contain motifs that are similar to the (E/D)FPPPPX(D/E) consensus sequence (SEQ ID NO:18) for EVH1 domain binding (the first conserved domain in the Ena/VASP family), the protein tyrosine phosphatases TPN22, PTPN1 (PTP1b), and the 5' inositol phosphatase INPPL1 (SHIP2). Of the three phosphatases identified, PTP1b and SHIP2 have been implicated in EGFR-mediated signaling responses. Highly-specific chemical inhibitors of SHIP2 or PTP1b were employed to determine their roles in Mena$^{INV}$-enhanced membrane protrusion. Inhibition of SHIP2 catalytic activity with AS1949490 reduced the protrusion response of MDA-MB231-GFPMena.sup.INV and MTLn3-GFP-Mena.sup.INV cells to levels measured in GFP control cells at 8 min poststimulation with 0.25 and 0.5 nM EGF, respectively (FIG. 8A, C). However, a kinetic analysis of protrusion revealed that in the presence of AS1949490, Mena$^{INV}$-expressing cells still demonstrated the fast initial protrusion response characteristic of Mena$^{INV}$ expressing-cells until after 3 min post-stimulation, when protrusion was abrogated (FIG. 8B, D). These data suggest that although SHIP2 activity is important for later stages of EGF driven lamellipodial protrusion, it is does not facilitate the Mena$^{INV}$ induced actin polymerization kinetics.

In contrast, inhibition of PTP1b increased lamellipodial protrusion in MDA-MB231-GFP control cells in a time dependent manner in response to 0.5 nM EGF. A 30 min pre-incubation of cells with inhibitor led to a complete phenocopy of Mena$^{INV}$-dependent responses in control cells, but had no effect on cells expressing Mena$^{INV}$ (FIG. 2A). More importantly, inhibition of PTP1b increased the kinetics of protrusion in MDA-MB231-GFP control cells without affecting the dynamics of MDA-MB231-GFP-Mena$^{INV}$ cells (FIG. 2B). Addition of the PTP1b inhibitor increased membrane protrusion in response to 0.25 nM EGF by both MDA-MB231-GFP-Mena and control cells expressing GFP, but not in MDA-MB231-GFP-Mena$^{INV}$ cells, indicating that dysregulation of PTP1b mimics inclusion of the INV exon but cannot provoke responses of greater magnitude in cells expressing Mena$^{INV}$ (FIG. 2C). PTP1b inhibition also increased the magnitude and kinetics of membrane protrusion in unmodified MTLn3 cells in response to 5 nM EGF, illustrating that the effect of PTP1b inhibition is not cell type dependent nor an artifact of retroviral transduction (FIG. 2D). Further, PTP1b inhibition does not increase membrane protrusion in cells expressing Mena$^{INV}$ in response to 0.125 nM EGF, a concentration that does not elicit a significant membrane protrusion response or EGFR activation in Mena$^{INV}$-expressing cells, suggesting that PTP1b inhibition alone is not sufficient to drive membrane protrusion in the absence of EGFR activation (data not shown).

It was next asked if decreased PTP1b activity affected tumor cell invasion. Inhibition of PTP1b increased MDA-MB231-GFP and GFP-Mena invasion into collagen I gels when stimulated with 0.25 or 0.5 nM EGF, but had no significant effect on cells expressing Mena$^{INV}$ (FIG. 2E, F). Expression of Mena$^{INV}$ decreases the concentration of EGF required for efficient chemotaxis/invasion by 25-fold in vivo [12]. Therefore, it was hypothesized that, similar to expression of Mena$^{INV}$, inhibition of PTP1b would increase the sensitivity of cells to EGF in vivo.

Figure 2G:
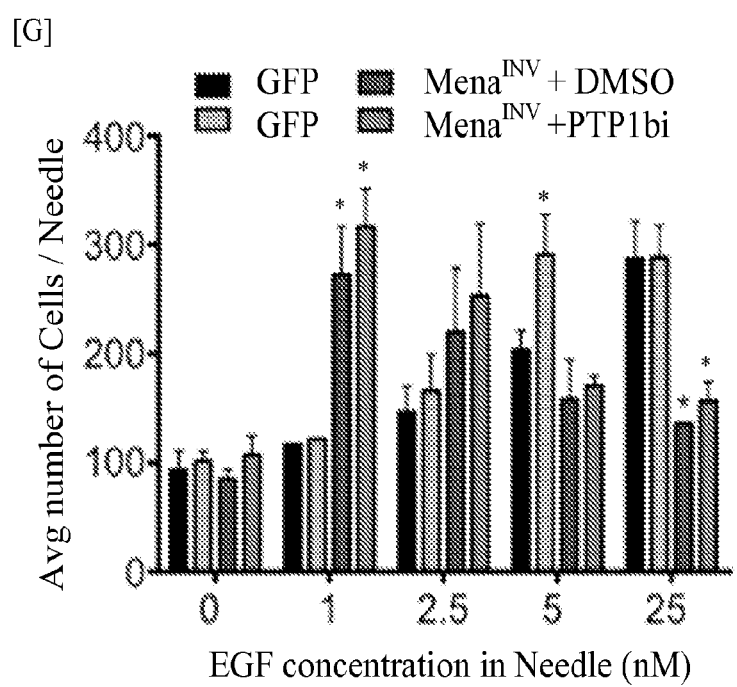

An in vivo invasion assay was employed to determine the effect of decreased PTP1b activity on tumor cell chemotaxis. To mimic the in vitro invasion experiments, 50 µM PTP1b inhibitor was added to needles with 10% matrigel and varying concentrations of EGF, the needles inserted into xenograft tumors of MTLn3 cells expressing either GFP or GFP-Mena$^{INV}$ and cells allowed to crawl into the needle during a 4 h period. Similar to the results obtained in vitro, addition of PTP1b inhibitor to needles used to collect cells had no effect on the number of cells ectopically expressing Mena$^{INV}$ collected (FIG. 2G). However, PTP1b inhibition increased the sensitivity of control cells 5-fold, decreasing the concentration of EGF required for chemotaxis into the needles from 25 nM to 5 nM. In this assay the discrepancy between expression of Mena$^{INV}$ and inhibition of PTP1b may be due to the time lag required for inhibitor efficacy.

However, viability of the mouse under anesthesia precludes collection of cells for longer periods than 4 h, therefore this effect is difficult to quantify. Taken together, these data indicate that inhibition of the protein tyrosine phosphatase PTP1b mimics the effects of Mena$^{INV}$ expression in cell motility in vitro and in vivo.

Figures 9A, 9B, 9C:
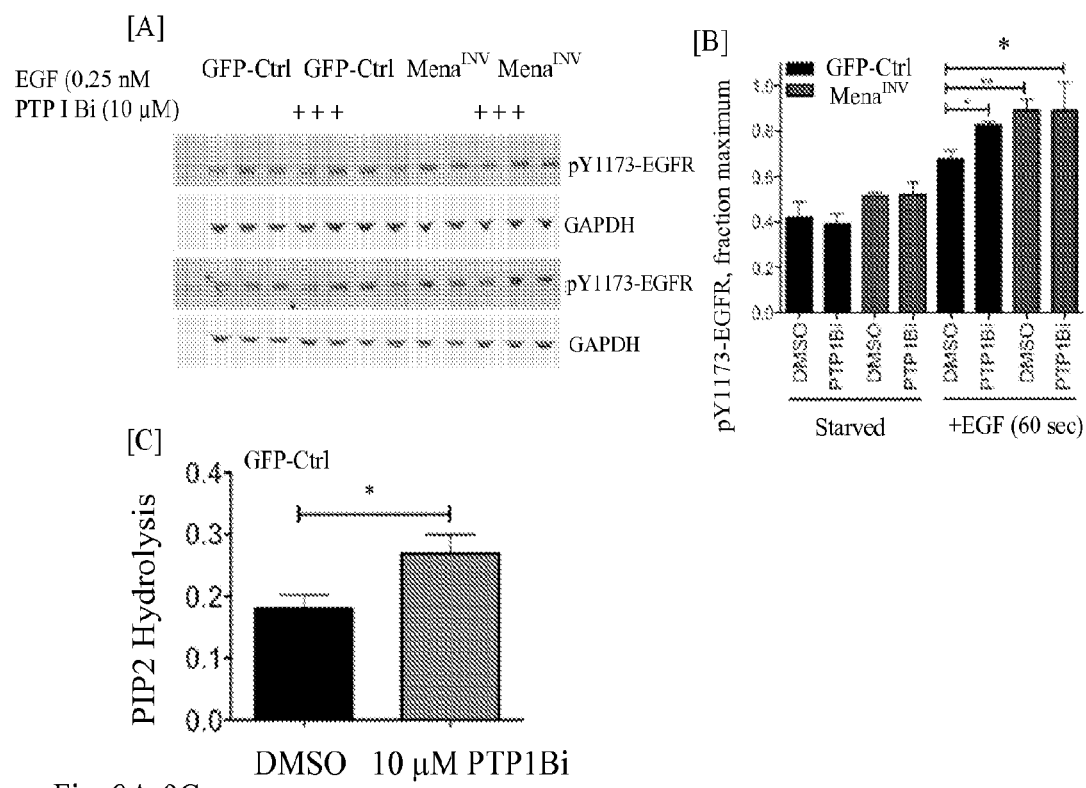
FIG. 9A-9C: PTP1b inhibition increases EGFR pathway activation. MDA-MB231 cells expressing GFP-control or GFPMena$^{INV}$ were serum starved for 4 h and stimulated with 0.25 nM EGF in the presence or absence of 10 µM PTP1b (30 min preincubation). Phosphorylation of EGFR on Y1173 was measured using semi-quantitative Western blotting (A, B) of quadruplicate lysates Inhibition of PTP1b increased EGFR Y1173 phosphorylation in cells expressing GFP-control, but not those expressing Mena$^{INV}$ (B). MTLn3 cells were transiently transfected with a mCherry-tagged PHdomain biosensor targeting PI(4,5)P2, starved in L15 media, pre-incubated with 10 µM PTP1bi and then stimulated with 0.5 nM EGF. The decrease in mCherry signal (as a fraction of the total signal at t=0 sec) is shown in (C) and indicates that PLCγ activity is greater in PTP1b inhibited GFP-control cells versus pre-incubation with DMSO.

Using MDA-MB231 cells, it was found that inhibition of PTP1b increased EGFR Y1173 phosphorylation in GFP control cells treated with 0.25 nM EGF, but had no additional affect on GFR phosphorylation in cells expressing Mena$^{INV}$ (FIG. 9A, B). Additionally, in MTLn3 cells, PTP1b inhibition increased PI(4,5)P2 hydrolysis at 3 min post-EGF stimulation (FIG. 9C), suggesting an increase in PLCγ activity similar to that exhibited by cells expressing Mena$^{INV}$.

Figures 3A, 3B:
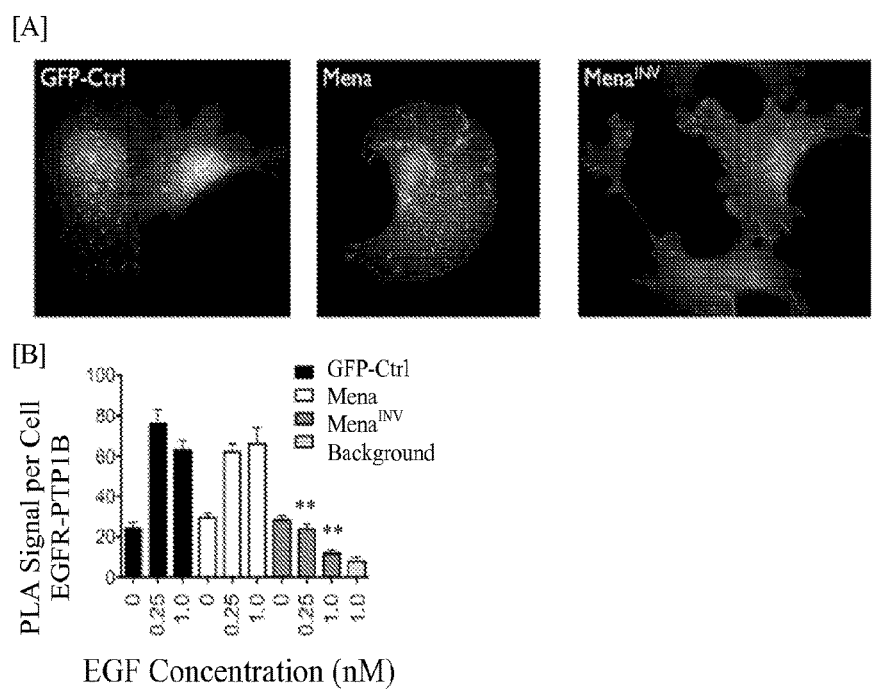
FIGS. 3A-B. Expression of Mena$^{INV}$ disrupts EGFR-PTP1b interaction. (A) MDA-MB231 cells were starved and stimulated with EGF for 60 sec before being fixed with 4% paraformaldehyde and processed for PLA (see text for detailed description). Light dots indicate an EGFR-PTP1b complex. Background refers to a control in which only an anti-EGFR antibody was employed. (B) The number of EGFR-PTP1b complexes increases in GFP-control and GFP-Mena expressing cells upon EGF stimulation, but not in cells that express GFP-Mena$^{INV}$. In (A), gray is actin and GFP, and light dots are PLA events. **p<0.01 using ANOVA with Tukey post-processing test.

The bioinformatic screening approach led to significant progress towards understanding how the expression of the INV exon leads to increased EGF sensitivity in invasive breast carcinoma. The expression of Mena$^{INV}$ leads to dysregulation of PTP1b, which in turn increases the flux through the EGF-initiated signaling network leading to actin polymerization and subsequent cell invasion. One possible mechanism of how Mena$^{INV}$ expression dysregulates PTP1b is through the disruption of PTP1b-EGFR interaction, as EGFR is a direct substrate of PTP1b activity. To test if Mena$^{INV}$ expression prevents PTP1b-EGFR interaction, a proximity ligation association (PLA, Olink Inc.) assay was employed a (FIG. 3). In this assay, MDA-MB231 or BT549 (data not shown) cells expressing GFP-control, GFP-Mena, or GFP-Mena$^{INV}$ are serum starved and then stimulated with 0.25 or 1.0 nM EGF for 60 sec. The cells are then fixed in 4% paraformaldehyde and stained with anti-PTP1b and anti-EGFR antibodies, similar to a normal indirect Immunofluorescence assay. However, instead of employing fluorescent secondary antibodies, two complementary oligoconjugated secondary antibodies are utilized. After incubation with the oligo-conjugated secondary antibodies, ligation and amplification steps are performed in situ. If PTP1b and EGFR are within 40 nm proximity, the oligos will anneal and incorporation of a fluorescent dye reveals the complex formation (the distance of 40 nm is to long to state that the pair directly interact). The number of events is quantified by counting the fluorescent dots (FIG. 3A). After serum starvation all cell lines (GFP-control, GFP-Mena, and GFP-Mena$^{INV}$) exhibit comparable numbers of EGFR-PTP1b complexes (FIG. 3B). Upon EGF stimulation, the number of complexes formed in GFP-control and GFPMena cells significantly increases, suggesting association between EGFR and PTP1b. It is likely that this interaction controls the level of EGFR phosphorylation, as inhibition of PTP1b increases EGFR phosphorylation at these EGF concentrations. However, in cells that express Mena$^{INV}$ the number of EGFR-PTP1b complexes does not increase upon EGF stimulation (FIG. 3B). Therefore, Mena$^{INV}$ increases EGFR activation by disrupting the complex that forms between EGFR and PTP1b.

Figures 10A, 10B:
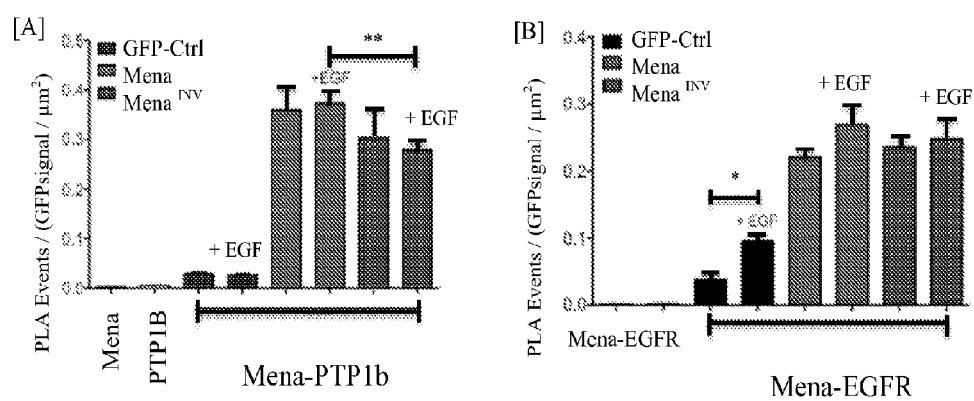
FIG. 10A-10B: Mena is located within complexes that contain PTP1b and EGFR. PLA was utilized to investigate complex formation between Mena and PTP1b (A) and Mena and EGFR (B) in serum-starved or 0.25 nM EGF-stimulated MDA-MB231 cells. The expression of Mena$^{INV}$ significantly decreases the number of EGF-independent Mena-PTP1b complexes formed (A). Conversely, Mena$^{INV}$ has no effect versus Mena alone on the number of Mena-EGFR complexes within the cell. However, expression of ectopic Mena or Mena$^{INV}$ abrogates complex formation in response to EGF (B).

To investigate how Mena$^{INV}$ disrupts the EGFR-PTP1b interaction, peptide array spot blots (FIG. 1A), GST-EVH1 pull down assay (FIG. 1B) and Proximity Ligation Assay (FIG. 1C) are used in unmodified MDA-MB231 cells that PTP1b and Mena exist in an EGF-independent protein complex, and likely bind directly. Expression of GFP-Mena increases the number of PTP1b-Mena complexes within the cell versus expression of a GFPcontrol construct (FIG. 10A). However, expression of Mena$^{INV}$ significantly decreases the number of PTP1b-Mena complexes within the cell versus ectopic expression of Mena alone (FIG. 10A). It was also found that Mena and EGFR exist within a complex (FIG. 10B). The Mena-EGFR complex is inducible by EGF in GFP-control cells, but the number of complexes is saturated upon ectopic expression of GFP-Mena or GFP-Mena$^{INV}$.

In sum, expression of Mena$^{INV}$ disrupts the interaction between EGFR and PTP1b, increasing the sensitivity of the EGFR-mediated intracellular signaling network resulting in enhanced actin polymerization and tumor cell invasion. Additionally, Mena can directly bind PTP1b and exists within a complex with EGFR.

Using phosphotyrosine mass spectrometry to study the alteration in the EGF-induced signaling pathways across GFP-control and GFPMena$^{INV}$-expressing cells, tyrosine-phosphorylated proteins (in duplicate) have been identified that have >25% increase in phosphorylation in cells expressing Mena$^{INV}$ versus GFP-control upon stimulation with 0.25 nM EGF for 60 sec. Of these, seven are literature reported substrates of PTP1b; Cdk2, EGFR, Intersectin 2, Paxillin, SHIP2 (IPPL1), SHB, and ZO-2. SHIP2 is a direct interacting partner of Mena and that SHIP2 interacts with EGFR through binding of Shc, which is phosphorylated by Y1173 of EGFR. It is hypothesized that SHIP2 mediates the complex formation between Mena and EGFR. Therefore, interruption of binding of SHIP2 and Mena$^{INV}$ could fail to bring PTP1b to the receptor, resulting in the disruption of EGFR-PTP1b interaction and accounting for the Mena$^{INV}$ phenotypes.

Figure 11:
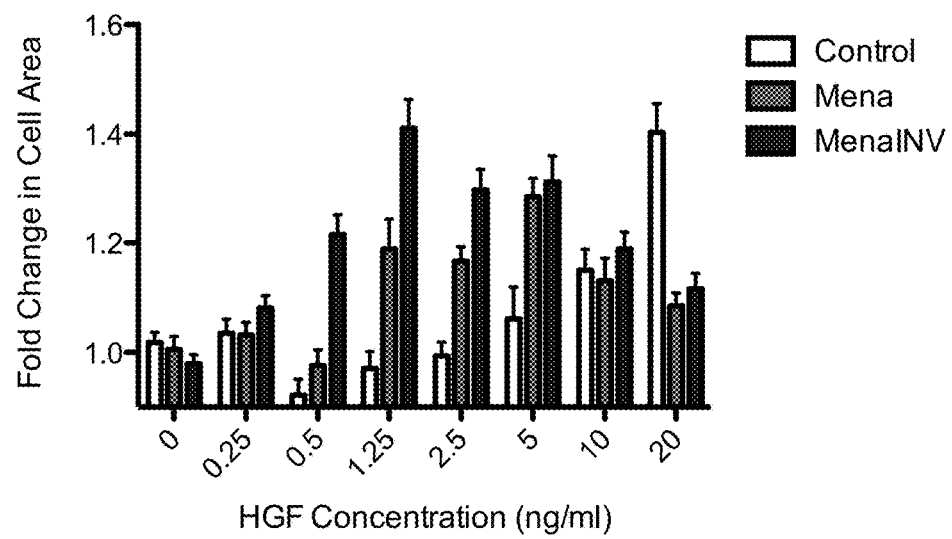
FIG. 11: Cell protrusion assays were performed in which starved carcinoma cells expressing GFP, GFP-Mena or GFP-Mena$^{INV}$ were stimulated with different concentrations of hepatocyte growth factor (HGF) (analogously as done with EGF stimulation of EGFR) followed by a measurement of cell protrusion several minutes later. The HGF concentrations (x-axis) are nM and the Y-axis is increase in cell size (a reflection of protrusion) compared to unstimulated cells.
Figure 12:
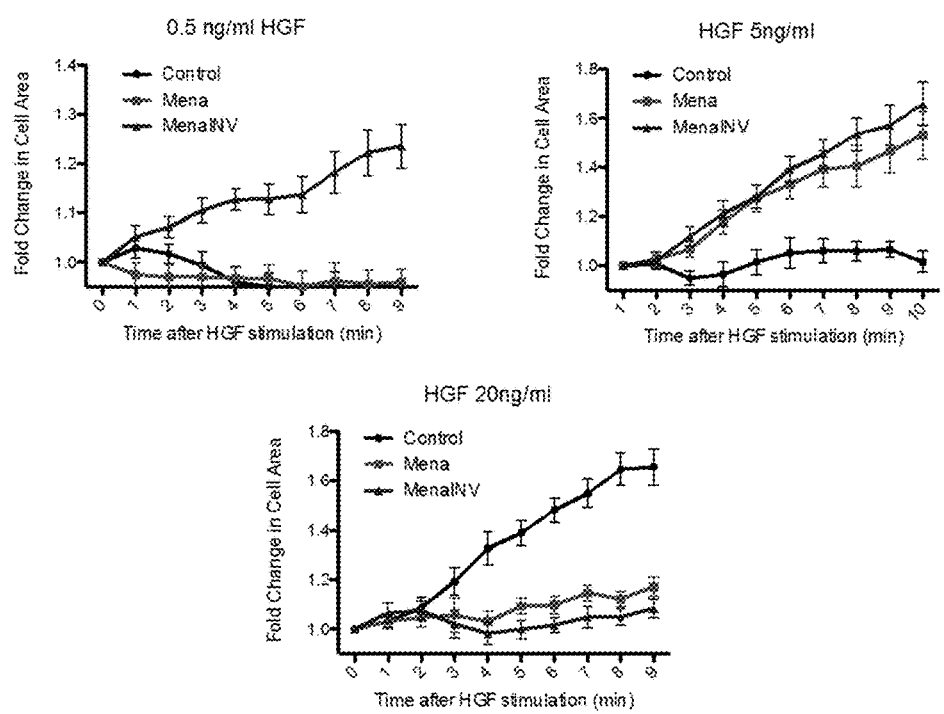
FIG. 12: Graphical representations of protrusion kinetics for different doses of HGF.
Figure 13:
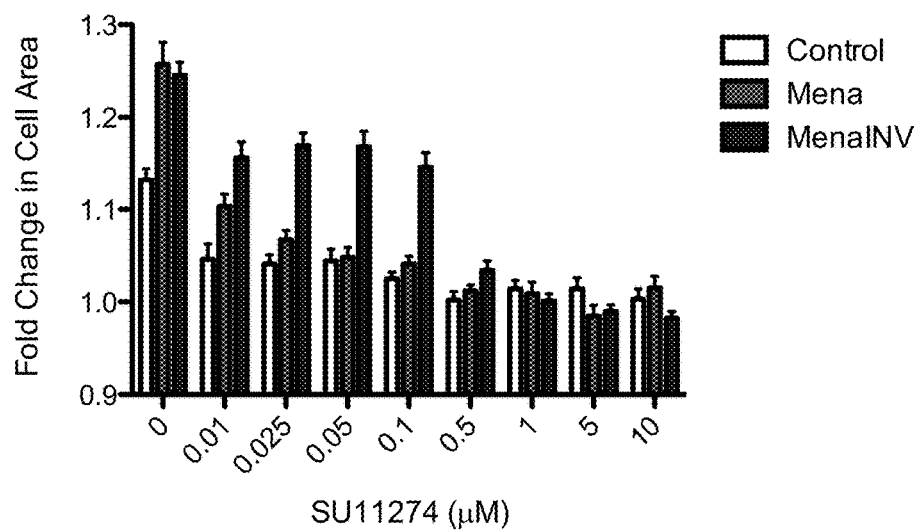
FIG. 13: Mena$^{INV}$ expressing cells are resistant to MET inhibitor in protrusion assay SU11274 (+5 ng/ml HGF).
Figure 14:
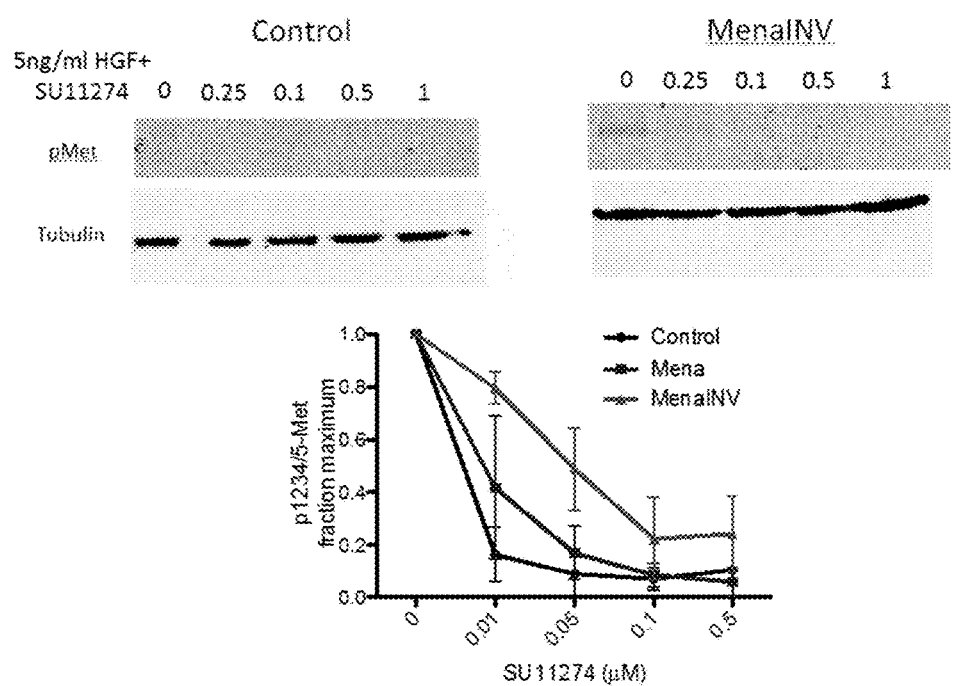
FIG. 14: Mena$^{INV}$ expressing cells are resistant to MET inhibitor-MET kinase activity.
Figure 15:
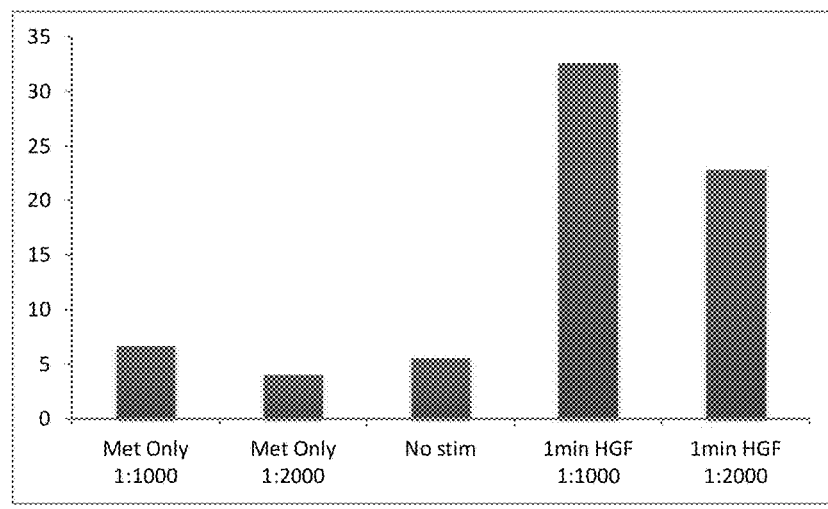
FIG. 15: As measured by PLA, HGF induces MET:PTP1B complexes (similar to the case with EGFR).
Figure 16:
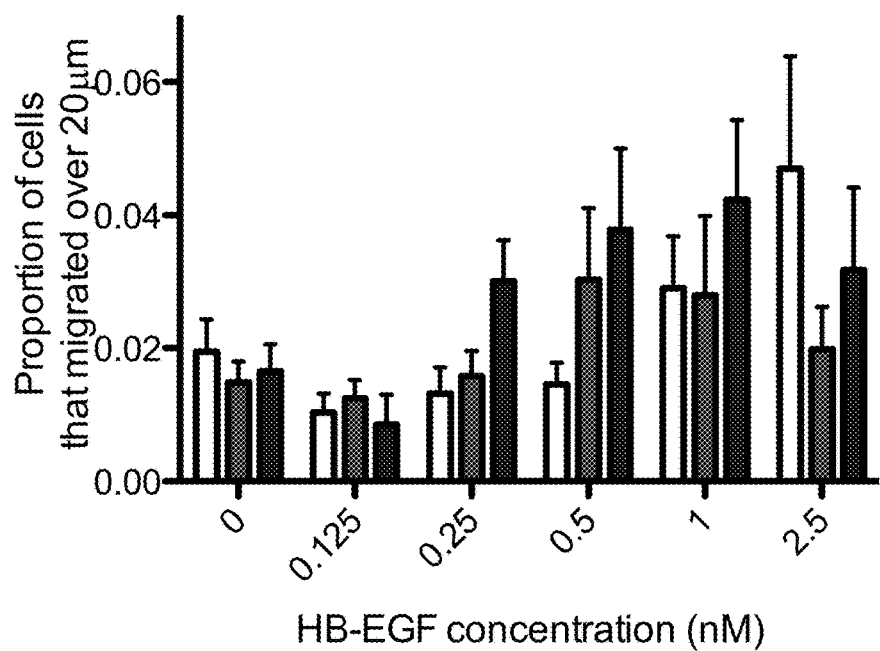
FIG. 16: 3D assay for HB-EGF.
Figure 17:
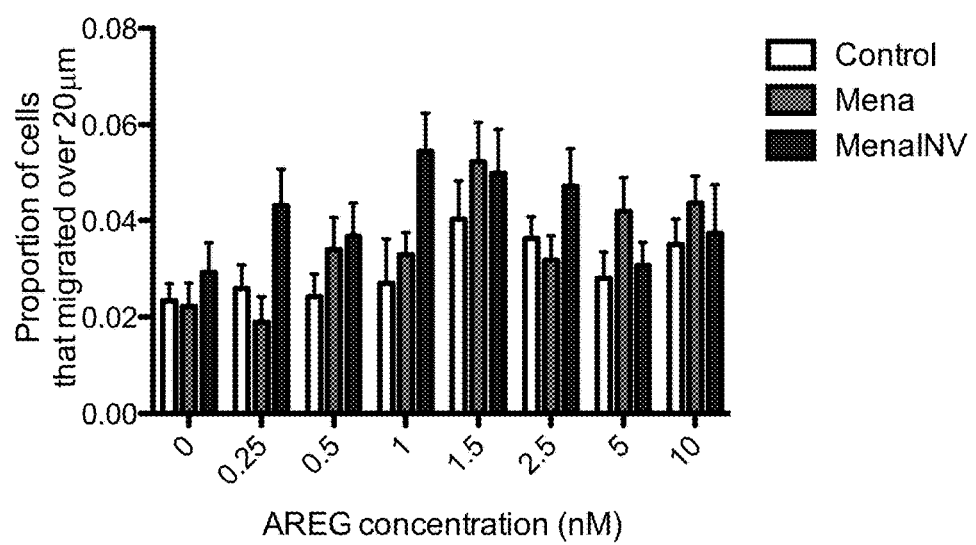
FIG. 17: 3D assay for AREG.
Figure 18:
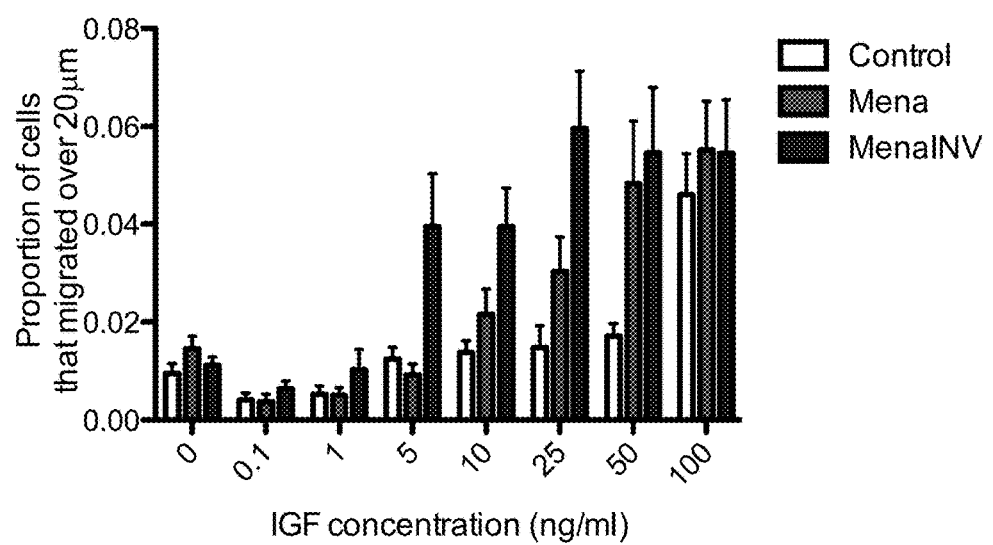
FIG. 18: 3D assay for IGF.
Figure 19:
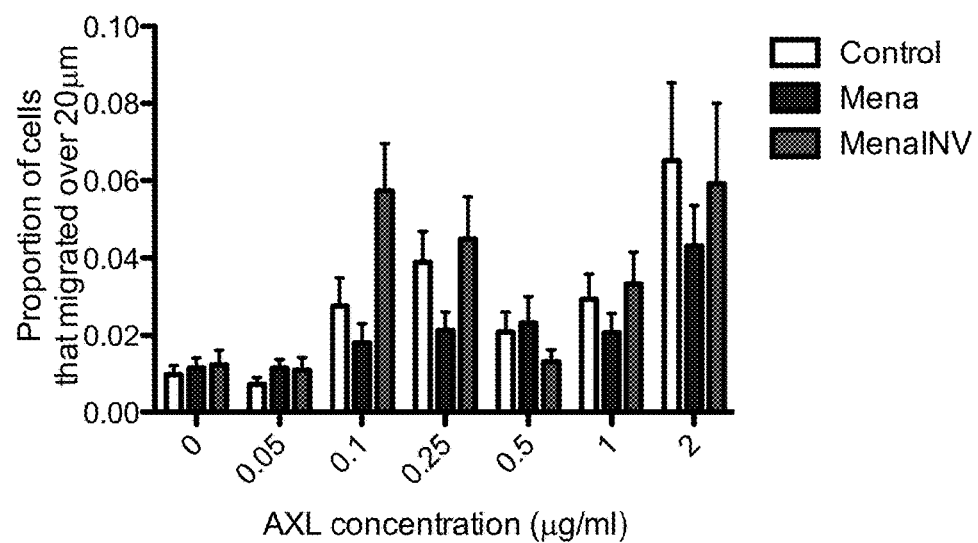
FIG. 19: 3D assay for AXL.

Further experimentation was performed to investigate the role of Mena$^{INV}$ with other growth factor receptors. As shown in FIG. 11, Mena$^{INV}$ has a striking effect on cell response to hepatocyte growth factor (HGF) stimulation of the MET receptor (the receptor encoded by c-Met, the hepatocyte growth factor receptor). Cell protrusion assays were performed in which starved carcinoma cells expressing GFP, GFP-Mena or GFP-Mena$^{INV}$ were stimulated with different concentrations of HGF (analogously as done with EGF stimulation of EGFR) followed by a measurement of cell protrusion several minutes later. At low HGF concentrations, Mena$^{INV}$-expressing cells can mount a significant protrusion response. For example, Mena$^{INV}$ cells stimulated with 1.25 nM HGF protruded as much as control cells stimulated with 20 nM, while Mena$^{INV}$ cells stimulated with 0.5 nM HGF protruded at a level similar to, or more than, control cells stimulated with 10 nM HGF. Since MET activity is implicated in metastatic progression of many tumor types, the effect of Mena$^{INV}$ is significant (see FIGS. 12-15 also), and its role in influencing anti-growth factor therapies, such as anti-HGFR therapies, is interesting and provides a therapeutic basis for enhancing such therapies. Notably, sensitization by Mena$^{INV}$ expression was also seen to IGF, AXL, HB-EGF, AREG and NRG (see FIGS. 16-19 also).

REFERENCES

1. Philippar, U., et al., *A Mena invasion isoform potentiates EGF-induced carcinoma cell invasion and metastasis.* Dev Cell, 2008. 15(6): p. 813-28.
2. Gertler, F. B., et al., *Mena, a relative of VASP and Drosophila Enabled, is implicated in the control of microfilament dynamics.* Cell, 1996. 87(2): p. 227-39.
3. Roussos, E. T., et al., *Mena invasive (Mena(INV)) and Mena11a isoforms play distinct roles in breast cancer cell cohesion and association with TMEM.* Clin Exp Metastasis, 2011. 28(6): p. 515-27.
4. Goswami, S., et al., *Identification of invasion specific splice variants of the cytoskeletal protein Mena present in mammary tumor cells during invasion in vivo.* Clin Exp Metastasis, 2009. 26(2): p. 153-9.

5. Soderberg, O., et al., *Characterizing proteins and their interactions in cells and tissues using the in situ proximity ligation assay*. Methods, 2008. 45(3): p. 227-32.

6. Haj, F. G., et al., *Regulation of receptor tyrosine kinase signaling by protein tyrosine phosphatase-1B*. J Biol Chem, 2003. 278(2): p. 739-44.

What is claimed is:

1. A method of enhancing the efficacy of an anti-hepatocyte growth factor receptor breast cancer therapy on a subject having breast cancer comprising administering to the subject an amount of an antibody, RNAi, aptamer or peptide inhibitor of Mena$^{INV}$ effective to enhance the efficacy of the anti-hepatocyte growth factor receptor breast cancer therapy administered to the subject.

2. The method of claim 1, wherein the therapy is cabozantinib therapy or foretinib therapy.

3. The method of claim 2, wherein the therapy is cabozantinib therapy.

4. The method of claim 2, wherein the therapy is foretinib therapy.

* * * * *

```
                          SEQUENCE LISTING

<160> NUMBER OF SEQ ID NOS: 18

<210> SEQ ID NO 1
<211> LENGTH: 25
<212> TYPE: PRT
<213> ORGANISM: HOMO SAPIENS

<400> SEQUENCE: 1

Ser Tyr Tyr Thr Val Arg Gln Leu Glu Leu Glu Asn Leu Thr Thr Gln
1               5                   10                  15

Glu Thr Arg Glu Ile Leu His Phe His
            20                  25

<210> SEQ ID NO 2
<211> LENGTH: 25
<212> TYPE: PRT
<213> ORGANISM: HOMO SAPIENS

<400> SEQUENCE: 2

Arg Gln Leu Glu Leu Glu Asn Leu Thr Thr Gln Glu Thr Arg Glu Ile
1               5                   10                  15

Leu His Phe His Tyr Thr Thr Trp Pro
            20                  25

<210> SEQ ID NO 3
<211> LENGTH: 25
<212> TYPE: PRT
<213> ORGANISM: HOMO SAPIENS

<400> SEQUENCE: 3

Glu Asn Leu Thr Thr Gln Glu Thr Arg Glu Ile Leu His Phe His Tyr
1               5                   10                  15

Thr Thr Trp Pro Asp Phe Gly Val Pro
            20                  25

<210> SEQ ID NO 4
<211> LENGTH: 25
<212> TYPE: PRT
<213> ORGANISM: HOMO SAPIENS

<400> SEQUENCE: 4

Gln Glu Thr Arg Glu Ile Leu His Phe His Tyr Thr Thr Trp Pro Asp
1               5                   10                  15

Phe Gly Val Pro Glu Ser Pro Ala Ser
            20                  25

<210> SEQ ID NO 5
<211> LENGTH: 25
<212> TYPE: PRT
<213> ORGANISM: HOMO SAPIENS

<400> SEQUENCE: 5

Ile Leu His Phe His Tyr Thr Thr Trp Pro Asp Phe Gly Val Pro Glu
1               5                   10                  15

Ser Pro Ala Ser Phe Leu Asn Phe Leu
            20                  25

<210> SEQ ID NO 6
```

```
<211> LENGTH: 25
<212> TYPE: PRT
<213> ORGANISM: HOMO SAPIENS

<400> SEQUENCE: 6

Tyr Thr Thr Trp Pro Asp Phe Gly Val Pro Glu Ser Pro Ala Ser Phe
1               5                   10                  15

Leu Asn Phe Leu Phe Lys Val Arg Glu
            20                  25

<210> SEQ ID NO 7
<211> LENGTH: 25
<212> TYPE: PRT
<213> ORGANISM: HOMO SAPIENS

<400> SEQUENCE: 7

Asp Phe Gly Val Pro Glu Ser Pro Ala Ser Phe Leu Asn Phe Leu Phe
1               5                   10                  15

Lys Val Arg Glu Ser Gly Ser Leu Ser
            20                  25

<210> SEQ ID NO 8
<211> LENGTH: 25
<212> TYPE: PRT
<213> ORGANISM: HOMO SAPIENS

<400> SEQUENCE: 8

Ile Met Gly Asp Ser Ser Val Gln Asp Gln Trp Lys Glu Leu Ser His
1               5                   10                  15

Glu Asp Leu Glu Pro Pro Pro Glu His
            20                  25

<210> SEQ ID NO 9
<211> LENGTH: 25
<212> TYPE: PRT
<213> ORGANISM: HOMO SAPIENS

<400> SEQUENCE: 9

Ser Val Gln Asp Gln Trp Lys Glu Leu Ser His Glu Asp Leu Glu Pro
1               5                   10                  15

Pro Pro Glu His Ile Pro Pro Pro
            20                  25

<210> SEQ ID NO 10
<211> LENGTH: 25
<212> TYPE: PRT
<213> ORGANISM: HOMO SAPIENS

<400> SEQUENCE: 10

Trp Lys Glu Leu Ser His Glu Asp Leu Glu Pro Pro Pro Glu His Ile
1               5                   10                  15

Pro Pro Pro Arg Pro Pro Lys Arg
            20                  25

<210> SEQ ID NO 11
<211> LENGTH: 25
<212> TYPE: PRT
<213> ORGANISM: HOMO SAPIENS

<400> SEQUENCE: 11

His Glu Asp Leu Glu Pro Pro Pro Glu His Ile Pro Pro Pro Arg
1               5                   10                  15
```

```
Pro Pro Lys Arg Ile Leu Glu Pro His
            20                  25

<210> SEQ ID NO 12
<211> LENGTH: 25
<212> TYPE: PRT
<213> ORGANISM: HOMO SAPIENS

<400> SEQUENCE: 12

Pro Pro Pro Glu His Ile Pro Pro Pro Arg Pro Pro Lys Arg Ile
1               5                   10                  15

Leu Glu Pro His Asn Gly Lys Cys Arg
            20                  25

<210> SEQ ID NO 13
<211> LENGTH: 25
<212> TYPE: PRT
<213> ORGANISM: HOMO SAPIENS

<400> SEQUENCE: 13

Ile Pro Pro Pro Pro Arg Pro Pro Lys Arg Ile Leu Glu Pro His Asn
1               5                   10                  15

Gly Lys Cys Arg Glu Phe Phe Pro Asn
            20                  25

<210> SEQ ID NO 14
<211> LENGTH: 25
<212> TYPE: PRT
<213> ORGANISM: HOMO SAPIENS

<400> SEQUENCE: 14

Ala Ser Asp Phe Pro Pro Pro Thr Asp Glu Glu Leu Arg Leu Ala
1               5                   10                  15

Leu Pro Glu Thr Pro Met Leu Leu Gly
            20                  25

<210> SEQ ID NO 15
<211> LENGTH: 19
<212> TYPE: PRT
<213> ORGANISM: HOMO SAPIENS

<400> SEQUENCE: 15

Ala Gln Ser Lys Val Thr Ala Thr Gln Asp Ser Thr Asn Leu Arg Cys
1               5                   10                  15

Ile Phe Cys

<210> SEQ ID NO 16
<211> LENGTH: 57
<212> TYPE: DNA
<213> ORGANISM: HOMO SAPIENS

<400> SEQUENCE: 16
gcccagagca aggttactgc tacccaggac agcactaatt tgcgatgtat tttctgt        57

<210> SEQ ID NO 17
<211> LENGTH: 1258
<212> TYPE: PRT
<213> ORGANISM: HOMO SAPIENS

<400> SEQUENCE: 17

Met Ala Ser Ala Cys Gly Ala Pro Gly Pro Gly Gly Ala Leu Gly Ser
1               5                   10                  15
```

```
Gln Ala Pro Ser Trp Tyr His Arg Asp Leu Ser Arg Ala Ala Ala Glu
            20                  25                  30

Glu Leu Leu Ala Arg Ala Gly Arg Asp Gly Ser Phe Leu Val Arg Asp
            35                  40                  45

Ser Glu Ser Val Ala Gly Ala Phe Ala Leu Cys Val Leu Tyr Gln Lys
        50                  55                  60

His Val His Thr Tyr Arg Ile Leu Pro Asp Gly Glu Asp Phe Leu Ala
65                  70                  75                  80

Val Gln Thr Ser Gln Gly Val Pro Val Arg Arg Phe Gln Thr Leu Gly
                85                  90                  95

Glu Leu Ile Gly Leu Tyr Ala Gln Pro Asn Gln Gly Leu Val Cys Ala
            100                 105                 110

Leu Leu Leu Pro Val Glu Gly Glu Arg Glu Pro Asp Pro Pro Asp Asp
            115                 120                 125

Arg Asp Ala Ser Asp Gly Glu Asp Glu Lys Pro Pro Leu Pro Pro Arg
130                 135                 140

Ser Gly Ser Thr Ser Ile Ser Ala Pro Thr Gly Pro Ser Ser Pro Leu
145                 150                 155                 160

Pro Ala Pro Glu Thr Pro Thr Ala Pro Ala Glu Ser Ala Pro Asn
                165                 170                 175

Gly Leu Ser Thr Val Ser His Asp Tyr Leu Lys Gly Ser Tyr Gly Leu
            180                 185                 190

Asp Leu Glu Ala Val Arg Gly Gly Ala Ser His Leu Pro His Leu Thr
            195                 200                 205

Arg Thr Leu Ala Thr Ser Cys Arg Arg Leu His Ser Glu Val Asp Lys
210                 215                 220

Val Leu Ser Gly Leu Glu Ile Leu Ser Lys Val Phe Asp Gln Gln Ser
225                 230                 235                 240

Ser Pro Met Val Thr Arg Leu Leu Gln Gln Gln Asn Leu Pro Gln Thr
                245                 250                 255

Gly Glu Gln Glu Leu Glu Ser Leu Val Leu Lys Leu Ser Val Leu Lys
            260                 265                 270

Asp Phe Leu Ser Gly Ile Gln Lys Lys Ala Leu Lys Ala Leu Gln Asp
            275                 280                 285

Met Ser Ser Thr Ala Pro Pro Ala Pro Gln Pro Ser Thr Arg Lys Ala
290                 295                 300

Lys Thr Ile Pro Val Gln Ala Phe Glu Val Lys Leu Asp Val Thr Leu
305                 310                 315                 320

Gly Asp Leu Thr Lys Ile Gly Lys Ser Gln Lys Phe Thr Leu Ser Val
                325                 330                 335

Asp Val Glu Gly Gly Arg Leu Val Leu Leu Arg Arg Gln Arg Asp Ser
            340                 345                 350

Gln Glu Asp Trp Thr Thr Phe Thr His Asp Arg Ile Arg Gln Leu Ile
            355                 360                 365

Lys Ser Gln Arg Val Gln Asn Lys Leu Gly Val Val Phe Glu Lys Glu
        370                 375                 380

Lys Asp Arg Thr Gln Arg Lys Asp Phe Ile Phe Val Ser Ala Arg Lys
385                 390                 395                 400

Arg Glu Ala Phe Cys Gln Leu Leu Gln Leu Met Lys Asn Lys His Ser
                405                 410                 415

Lys Gln Asp Glu Pro Asp Met Ile Ser Val Phe Ile Gly Thr Trp Asn
            420                 425                 430

Met Gly Ser Val Pro Pro Pro Lys Asn Val Thr Ser Trp Phe Thr Ser
```

```
              435                 440                 445
Lys Gly Leu Gly Lys Thr Leu Asp Glu Val Thr Val Thr Ile Pro His
450                 455                 460

Asp Ile Tyr Val Phe Gly Thr Gln Glu Asn Ser Val Gly Asp Arg Glu
465                 470                 475                 480

Trp Leu Asp Leu Leu Arg Gly Gly Leu Lys Glu Leu Thr Asp Leu Asp
                485                 490                 495

Tyr Arg Pro Ile Ala Met Gln Ser Leu Trp Asn Ile Lys Val Ala Val
                500                 505                 510

Leu Val Lys Pro Glu His Glu Asn Arg Ile Ser His Val Ser Thr Ser
                515                 520                 525

Ser Val Lys Thr Gly Ile Ala Asn Thr Leu Gly Asn Lys Gly Ala Val
530                 535                 540

Gly Val Ser Phe Met Phe Asn Gly Thr Ser Phe Gly Phe Val Asn Cys
545                 550                 555                 560

His Leu Thr Ser Gly Asn Glu Lys Thr Ala Arg Arg Asn Gln Asn Tyr
                565                 570                 575

Leu Asp Ile Leu Arg Leu Leu Ser Leu Gly Asp Arg Gln Leu Asn Ala
                580                 585                 590

Phe Asp Ile Ser Leu Arg Phe Thr His Leu Phe Trp Phe Gly Asp Leu
                595                 600                 605

Asn Tyr Arg Leu Asp Met Asp Ile Gln Glu Ile Leu Asn Tyr Ile Ser
                610                 615                 620

Arg Lys Glu Phe Glu Pro Leu Leu Arg Val Asp Gln Leu Asn Leu Glu
625                 630                 635                 640

Arg Glu Lys His Lys Val Phe Leu Arg Phe Ser Glu Glu Ile Ser
                645                 650                 655

Phe Pro Pro Thr Tyr Arg Tyr Glu Arg Gly Ser Arg Asp Thr Tyr Ala
                660                 665                 670

Trp His Lys Gln Lys Pro Thr Gly Val Arg Thr Asn Val Pro Ser Trp
                675                 680                 685

Cys Asp Arg Ile Leu Trp Lys Ser Tyr Pro Glu Thr His Ile Ile Cys
690                 695                 700

Asn Ser Tyr Gly Cys Thr Asp Asp Ile Val Thr Ser Asp His Ser Pro
705                 710                 715                 720

Val Phe Gly Thr Phe Glu Val Gly Val Thr Ser Gln Phe Ile Ser Lys
                725                 730                 735

Lys Gly Leu Ser Lys Thr Ser Asp Gln Ala Tyr Ile Glu Phe Glu Ser
                740                 745                 750

Ile Glu Ala Ile Val Lys Thr Ala Ser Arg Thr Lys Phe Phe Ile Glu
                755                 760                 765

Phe Tyr Ser Thr Cys Leu Glu Glu Tyr Lys Lys Ser Phe Glu Asn Asp
                770                 775                 780

Ala Gln Ser Ser Asp Asn Ile Asn Phe Leu Lys Val Gln Trp Ser Ser
785                 790                 795                 800

Arg Gln Leu Pro Thr Leu Lys Pro Ile Leu Ala Asp Ile Glu Tyr Leu
                805                 810                 815

Gln Asp Gln His Leu Leu Leu Thr Val Lys Ser Met Asp Gly Tyr Glu
                820                 825                 830

Ser Tyr Gly Glu Cys Val Val Ala Leu Lys Ser Met Ile Gly Ser Thr
                835                 840                 845

Ala Gln Gln Phe Leu Thr Phe Leu Ser His Arg Gly Glu Glu Thr Gly
850                 855                 860
```

```
Asn Ile Arg Gly Ser Met Lys Val Arg Val Pro Thr Glu Arg Leu Gly
865                 870                 875                 880

Thr Arg Glu Arg Leu Tyr Glu Trp Ile Ser Ile Asp Lys Asp Glu Ala
                885                 890                 895

Gly Ala Lys Ser Lys Ala Pro Ser Val Ser Arg Gly Ser Gln Glu Pro
            900                 905                 910

Arg Ser Gly Ser Arg Lys Pro Ala Phe Thr Glu Ala Ser Cys Pro Leu
        915                 920                 925

Ser Arg Leu Phe Glu Glu Pro Glu Lys Pro Pro Thr Gly Arg Pro
    930                 935                 940

Pro Ala Pro Pro Arg Ala Ala Pro Arg Glu Glu Pro Leu Thr Pro Arg
945                 950                 955                 960

Leu Lys Pro Glu Gly Ala Pro Glu Pro Glu Gly Val Ala Ala Pro Pro
                965                 970                 975

Pro Lys Asn Ser Phe Asn Asn Pro Ala Tyr Tyr Val Leu Gly Val
            980                 985                 990

Pro His Gln Leu Leu Pro Pro Glu Pro Pro Ser Pro Ala Arg Ala Pro
        995                 1000                1005

Val Pro Ser Ala Thr Lys Asn Lys Val Ala Ile Thr Val Pro Ala
    1010                1015                1020

Pro Gln Leu Gly His His Arg His Pro Arg Val Gly Glu Gly Ser
    1025                1030                1035

Ser Ser Asp Glu Glu Ser Gly Gly Thr Leu Pro Pro Pro Asp Phe
    1040                1045                1050

Pro Pro Pro Pro Leu Pro Asp Ser Ala Ile Phe Leu Pro Pro Ser
    1055                1060                1065

Leu Asp Pro Leu Pro Gly Pro Val Val Arg Gly Arg Gly Gly Ala
    1070                1075                1080

Glu Ala Arg Gly Pro Pro Pro Lys Ala His Pro Arg Pro Pro
    1085                1090                1095

Leu Pro Pro Gly Pro Ser Pro Ala Ser Thr Phe Leu Gly Glu Val
    1100                1105                1110

Ala Ser Gly Asp Asp Arg Ser Cys Ser Val Leu Gln Met Ala Lys
    1115                1120                1125

Thr Leu Ser Glu Val Asp Tyr Ala Pro Ala Gly Pro Ala Arg Ser
    1130                1135                1140

Ala Leu Leu Pro Gly Pro Leu Glu Leu Gln Pro Pro Arg Gly Leu
    1145                1150                1155

Pro Ser Asp Tyr Gly Arg Pro Leu Ser Phe Pro Pro Arg Ile
    1160                1165                1170

Arg Glu Ser Ile Gln Glu Asp Leu Ala Glu Glu Ala Pro Cys Leu
    1175                1180                1185

Gln Gly Gly Arg Ala Ser Gly Leu Gly Glu Ala Gly Met Ser Ala
    1190                1195                1200

Trp Leu Arg Ala Ile Gly Leu Glu Arg Tyr Glu Glu Gly Leu Val
    1205                1210                1215

His Asn Gly Trp Asp Asp Leu Glu Phe Leu Ser Asp Ile Thr Glu
    1220                1225                1230

Glu Asp Leu Glu Glu Ala Gly Val Gln Asp Pro Ala His Lys Arg
    1235                1240                1245

Leu Leu Leu Asp Thr Leu Gln Leu Ser Lys
    1250                1255
```

```
<210> SEQ ID NO 18
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: x = E or D
<220> FEATURE:
<221> NAME/KEY: MISC_FEATURE
<222> LOCATION: (7)..(7)
<223> OTHER INFORMATION: x = any amino acid
<220> FEATURE:
<221> NAME/KEY: MISC_FEATURE
<222> LOCATION: (8)..(8)
<223> OTHER INFORMATION: x = D or E

<400> SEQUENCE: 18

Xaa Phe Pro Pro Pro Pro Xaa Xaa
1               5
```